(12) United States Patent
Pulé et al.

(10) Patent No.: US 11,530,420 B2
(45) Date of Patent: Dec. 20, 2022

(54) NUCLEIC ACID CONSTRUCT

(71) Applicant: AUTOLUS LIMITED, London (GB)

(72) Inventors: Martin Pulé, London (GB); Shaun Cordoba, London (GB)

(73) Assignee: AUTOLUS LIMITED, London (GB)

( * ) Notice: Subject to any disclaimer, the term of this patent is extended or adjusted under 35 U.S.C. 154(b) by 0 days.

(21) Appl. No.: 15/568,859

(22) PCT Filed: Apr. 26, 2016

(86) PCT No.: PCT/GB2016/051164
§ 371 (c)(1),
(2) Date: Oct. 24, 2017

(87) PCT Pub. No.: WO2016/174408
PCT Pub. Date: Nov. 3, 2016

(65) Prior Publication Data
US 2018/0100163 A1 Apr. 12, 2018

(30) Foreign Application Priority Data
Apr. 27, 2015 (GB) .................................... 1507104

(51) Int. Cl.
*C12N 15/00* (2006.01)
*C12N 15/86* (2006.01)
*C07K 14/705* (2006.01)
*C07K 16/28* (2006.01)
*C12N 15/85* (2006.01)

(52) U.S. Cl.
CPC ........ *C12N 15/86* (2013.01); *C07K 14/70521* (2013.01); *C07K 14/70596* (2013.01); *C07K 16/2803* (2013.01); *C12N 15/85* (2013.01); *C07K 2317/622* (2013.01); *C07K 2319/03* (2013.01); *C07K 2319/04* (2013.01); *C07K 2319/06* (2013.01); *C07K 2319/33* (2013.01); *C07K 2319/50* (2013.01)

(58) Field of Classification Search
CPC .... C12N 15/86; C12N 15/85; C07K 2319/03; C07K 2319/04; C07K 2319/06; C07K 2319/50
See application file for complete search history.

(56) References Cited

U.S. PATENT DOCUMENTS

2016/0046700 A1* 2/2016 Foster ..................... A61P 25/00
424/134.1
2018/0009994 A1 4/2018 Pule et al.

FOREIGN PATENT DOCUMENTS

WO WO-2007014162 A2 * 2/2007 ............. C07K 16/00
WO WO-2013185552 A1 * 12/2013 ......... C07K 16/3092
WO WO-2014/079878 A1 5/2014

OTHER PUBLICATIONS

El Amrani in "Coordinate Expression and Independent Subcellular Targeting of Multiple Proteins from a Single Transgene" (Plant Physiology 2004 vol. 135, No. 1: pp. 16-24: IDS reference (Year: 2004).*
Goder and Spiess entitled "Topogenesis of membrane proteins: determinants and dynamics" (FEBS Letters 2001 vol. 504:pp. 87-93; see especially abstract lines 11-14; IDS reference). (Year: 2001).*
Wilkie et al (J Clin Immunol (2012) 32:1059-1070) . (Year: 2012).*
Hiller et al (Nucleic Acids Res. 2004, W375-W379). (Year: 2004).*
De Felipe et al in "Skipping the co-expression problem: the new 2A CHYSEL technology" (Genetic Vaccines And Therapy, Biomed Central, London, Gb, vol. 2, No. 1, published Sep. 13, 2004, p. 13; IDS reference). (Year: 2004).*
Parmar et al "Polybasic Trafficking Signal Mediates Golgi Export, ER Retention or ER Export and Retrieval Based on Membrane-Proximity" (PLOS One, published Apr. 8, 2014). (Year: 2014).*
Singleton et al "The first transmembrane region of the beta-chain stabilizes the tetrameric Fcepsilon RI complex" ( Molecular Immunology vol. 46, pp. 2333-2339, published online Apr. 29, 2009). (Year: 2009).*
Pelham ("Using Sorting Signals to Retain Proteins in Endoplasmic Reticulum" Methods in Enzymology, vol. 327, pp. 279-283). (Year: 2000).*
Cordoba et al (Molecular Therapy, vol. 22, Supplement 1, May 1, 2014: S59). (Year: 2014).*
Parmaretal (PLOS ONE published Apr. 8, 2014; IDS reference). (Year: 2014).*
Bonifacino et al., Signals for sorting of transmembrane proteins to endosomes and lysosomes, Annu. Rev. Biochem., 72:395-447 (2003).
Braulke et al., Sorting of lysosomal proteins, Biochim. Biophys. Acta, 1793(4):605-14 (2009).
De Felipe et al., Inhibition of 2A-mediated 'cleavage' of certain artificial polyproteins bearing N-terminal signal sequences, Biotechnol. J., 5(2):213-23 (2010).
De Felipe et al., Targeting of proteins derived from self-processing polyproteins containing multiple signal sequences, Traffic, 5(8):616-26 (2004).
De Felipe, Skipping the co-expression problem: the new 2A "CHYSEL" technology, Genet. Vaccines Ther., 2(1):13 (2004).
Dell-Angelica et al., Intracellular cycling of lysosomal enzyme receptors: cytoplasmic tails' tales, Cell, 106(4):395-8 (2001).
Donnelly et al., The 'cleavage' activities of foot-and-mouth disease virus 2A site-directed mutants and naturally occurring '2A-like' sequences, J. Gen. Virol., 82(Pt. 5):1027-41 (2001).

(Continued)

*Primary Examiner* — Catherine S Hibbert
(74) *Attorney, Agent, or Firm* — Marshall, Gerstein & Borun LLP

(57) ABSTRACT

The present invention provides a nucleic acid construct comprising the following structure: A-X-B in which A and B are nucleic acid sequences encoding a first and a second polypeptide of interest (POI); and X is a nucleic acid sequence which encodes a cleavage site, wherein either the first or second POI is a transmembrane protein which comprises an intracellular retention signal.

19 Claims, 9 Drawing Sheets

Specification includes a Sequence Listing.

(56) References Cited

OTHER PUBLICATIONS

El Amrani et al., Coordinate expression and independent subcellular targeting of multiple proteins from a single transgene, Plant Physiol., 135(1):16-24 (2004).
Goder et al., Topogenesis of membrane proteins: determinants and dynamics, FEBS Lett., 504(3):87-93 (2001).
Griffith, Potassium channels: the importance of transport signals, Curr. Biol., 11 (6):R226-8 (2001).
International Application No. PCT/GB2014/051164, International Search Report and Written Opinion, dated Jul. 11, 2016.
Luke et al., Self-processing polyproteins: a strategy for co-expression of multiple proteins in plants, Biotechnol. Genet. Eng. Rev., 23:239-52 (2006).
Mellman et al., Coordinated protein sorting, targeting and distribution in polarized cells, Nat. Rev. Mol. Cell Biol., 9(11):833-45 (2008).
Pelham, Using sorting signals to retain proteins in endoplasmic reticulum, Methods Enzymol., 327:279-83 (2000).

Schäfer et al., Two independent targeting signals in the cytoplasmic domain determine trans-Golgi network localization and endosomal trafficking of the proprotein convertase furin, EMBO J., 14(11):2424-35 (1995).
Teasdale et al., Signal-mediated sorting of membrane proteins between the endoplasmic reticulum and the golgi apparatus, Annu. Rev. Cell Dev. Biol., 12:27-54 (1996).
Trejo, Internal PDZ ligands: novel endocytic recycling motifs for G protein-coupled receptors, Mol. Pharmacol., 67(5):1388-90 (2005).
Wilson et al., pH-dependent binding of KDEL to its receptor in vitro, J. Biol. Chem., 268:7465 (1993).
Ghanem et al., "Tyrosinase related protein 1 (TYRP1/gp75) in human cutaneous melanoma," 5:150-155 (2011).
International Search Report and Written Opinion from International Application No. PCT/GB2016/051164 dated Jul. 11, 2016.
McSharry et al., "Adenovirus E3/19K Promotes Evasion of NK Cell Recognition by Intracellular Sequestration of the NKG2D Ligands Major Histocompatibility Complex Class I Chain-Related Proteins A and B," Journal of Virology 82(9):4585-4594 (2008).

* cited by examiner

A

B

SEQUENCE LISTING

<160> NUMBER OF SEQ ID NOS: 197

<210> SEQ ID NO 1
<211> LENGTH: 8
<212> TYPE: PRT
<213> ORGANISM: Artificial Sequence
<220> FEATURE:
<223> OTHER INFORMATION: Cleavage site

<400> SEQUENCE: 1

Asp Ile Glu Thr Asn Pro Gly Pro
1               5

<210> SEQ ID NO 2
<211> LENGTH: 8
<212> TYPE: PRT
<213> ORGANISM: Artificial Sequence
<220> FEATURE:
<223> OTHER INFORMATION: Cleavage site

<400> SEQUENCE: 2

Asp Val Glu Thr Asn Pro Gly Pro
1               5

<210> SEQ ID NO 3
<211> LENGTH: 8
<212> TYPE: PRT
<213> ORGANISM: Artificial Sequence
<220> FEATURE:
<223> OTHER INFORMATION: Cleavage site

<400> SEQUENCE: 3

Asp Val Glu Met Asn Pro Gly Pro
1               5

<210> SEQ ID NO 4
<211> LENGTH: 8
<212> TYPE: PRT
<213> ORGANISM: Artificial Sequence
<220> FEATURE:
<223> OTHER INFORMATION: Cleavage site

<400> SEQUENCE: 4

Asp Val Glu Ser Asn Pro Gly Pro
1               5

<210> SEQ ID NO 5
<211> LENGTH: 8
<212> TYPE: PRT
<213> ORGANISM: Artificial Sequence
<220> FEATURE:
<223> OTHER INFORMATION: Cleavege site

<400> SEQUENCE: 5

Asp Met Glu Ser Asn Pro Gly Pro
1               5

<210> SEQ ID NO 6
<211> LENGTH: 8
<212> TYPE: PRT
<213> ORGANISM: Artificial Sequence
<220> FEATURE:
<223> OTHER INFORMATION: Cleavage site

<400> SEQUENCE: 6

Asp Val Glu Leu Asn Pro Gly Pro
1               5

```
<210> SEQ ID NO 7
<211> LENGTH: 8
<212> TYPE: PRT
<213> ORGANISM: Artificial Sequence
<220> FEATURE:
<223> OTHER INFORMATION: Cleavage site

<400> SEQUENCE: 7

Asp Val Glu Glu Asn Pro Gly Pro
1               5

<210> SEQ ID NO 8
<211> LENGTH: 8
<212> TYPE: PRT
<213> ORGANISM: Artificial Sequence
<220> FEATURE:
<223> OTHER INFORMATION: Cleavage site

<400> SEQUENCE: 8

Asp Ile Glu Leu Asn Pro Gly Pro
1               5

<210> SEQ ID NO 9
<211> LENGTH: 8
<212> TYPE: PRT
<213> ORGANISM: Artificial Sequence
<220> FEATURE:
<223> OTHER INFORMATION: Cleavage site

<400> SEQUENCE: 9

Asp Ile Glu Gln Asn Pro Gly Pro
1               5

<210> SEQ ID NO 10
<211> LENGTH: 8
<212> TYPE: PRT
<213> ORGANISM: Artificial Sequence
<220> FEATURE:
<223> OTHER INFORMATION: Cleavage site

<400> SEQUENCE: 10

Asp Ser Glu Phe Asn Pro Gly Pro
1               5

<210> SEQ ID NO 11
<211> LENGTH: 19
<212> TYPE: PRT
<213> ORGANISM: Artificial Sequence
<220> FEATURE:
<223> OTHER INFORMATION: Cleavage sequence

<400> SEQUENCE: 11

Leu Leu Asn Phe Asp Leu Leu Lys Leu Ala Gly Asp Val Glu Ser Asn
1               5                   10                  15

Pro Gly Pro

<210> SEQ ID NO 12
<211> LENGTH: 19
<212> TYPE: PRT
<213> ORGANISM: Artificial Sequence
<220> FEATURE:
<223> OTHER INFORMATION: Cleavage sequence

<400> SEQUENCE: 12

Leu Leu Asn Phe Asp Leu Leu Lys Leu Ala Gly Asp Val Gln Ser Asn
```

```
1               5                   10                  15

Pro Gly Pro

<210> SEQ ID NO 13
<211> LENGTH: 19
<212> TYPE: PRT
<213> ORGANISM: Artificial Sequence
<220> FEATURE:
<223> OTHER INFORMATION: Cleavage sequence

<400> SEQUENCE: 13

Leu Leu Asn Phe Asp Leu Leu Lys Leu Ala Gly Asp Val Glu Ile Asn
1               5                   10                  15

Pro Gly Pro

<210> SEQ ID NO 14
<211> LENGTH: 19
<212> TYPE: PRT
<213> ORGANISM: Artificial Sequence
<220> FEATURE:
<223> OTHER INFORMATION: Cleavage sequence

<400> SEQUENCE: 14

Leu Leu Asn Phe Asp Leu Leu Lys Leu Ala Gly Asp Val Glu Phe Asn
1               5                   10                  15

Pro Gly Pro

<210> SEQ ID NO 15
<211> LENGTH: 19
<212> TYPE: PRT
<213> ORGANISM: Artificial Sequence
<220> FEATURE:
<223> OTHER INFORMATION: Cleavage sequence

<400> SEQUENCE: 15

Leu Leu Asn Phe Asp Leu Leu Lys Leu Ala Gly Asp Val Glu Ser His
1               5                   10                  15

Pro Gly Pro

<210> SEQ ID NO 16
<211> LENGTH: 19
<212> TYPE: PRT
<213> ORGANISM: Artificial Sequence
<220> FEATURE:
<223> OTHER INFORMATION: Cleavage sequence

<400> SEQUENCE: 16

Leu Leu Asn Phe Asp Leu Leu Lys Leu Ala Gly Asp Val Glu Ser Glu
1               5                   10                  15

Pro Gly Pro

<210> SEQ ID NO 17
<211> LENGTH: 19
<212> TYPE: PRT
<213> ORGANISM: Artificial Sequence
<220> FEATURE:
<223> OTHER INFORMATION: Cleavage sequence

<400> SEQUENCE: 17

Leu Leu Asn Phe Asp Leu Leu Lys Leu Ala Gly Asp Val Glu Ser Gln
1               5                   10                  15

Pro Gly Pro
```

```
<210> SEQ ID NO 18
<211> LENGTH: 19
<212> TYPE: PRT
<213> ORGANISM: Artificial Sequence
<220> FEATURE:
<223> OTHER INFORMATION: Cleavage sequence

<400> SEQUENCE: 18

Leu Leu Asn Phe Asp Leu Leu Lys Leu Ala Gly Asp Val Glu Ser Asn
1               5                   10                  15

Pro Gly Gly

<210> SEQ ID NO 19
<211> LENGTH: 20
<212> TYPE: PRT
<213> ORGANISM: Artificial Sequence
<220> FEATURE:
<223> OTHER INFORMATION: Cleavage site, 2A-like sequence

<400> SEQUENCE: 19

Tyr His Ala Asp Tyr Tyr Lys Gln Arg Leu Ile His Asp Val Glu Met
1               5                   10                  15

Asn Pro Gly Pro
            20

<210> SEQ ID NO 20
<211> LENGTH: 20
<212> TYPE: PRT
<213> ORGANISM: Artificial Sequence
<220> FEATURE:
<223> OTHER INFORMATION: Cleavage site, 2A-like sequence

<400> SEQUENCE: 20

His Tyr Ala Gly Tyr Phe Ala Asp Leu Leu Ile His Asp Ile Glu Thr
1               5                   10                  15

Asn Pro Gly Pro
            20

<210> SEQ ID NO 21
<211> LENGTH: 20
<212> TYPE: PRT
<213> ORGANISM: Artificial Sequence
<220> FEATURE:
<223> OTHER INFORMATION: Cleavage site, 2A-like sequence

<400> SEQUENCE: 21

Gln Cys Thr Asn Tyr Ala Leu Leu Lys Leu Ala Gly Asp Val Glu Ser
1               5                   10                  15

Asn Pro Gly Pro
            20

<210> SEQ ID NO 22
<211> LENGTH: 19
<212> TYPE: PRT
<213> ORGANISM: Artificial Sequence
<220> FEATURE:
<223> OTHER INFORMATION: Cleavage site, 2A-like sequence

<400> SEQUENCE: 22

Ala Thr Asn Phe Ser Leu Leu Lys Gln Ala Gly Asp Val Glu Glu Asn
1               5                   10                  15

Pro Gly Pro
```

```
<210> SEQ ID NO 23
<211> LENGTH: 19
<212> TYPE: PRT
<213> ORGANISM: Artificial Sequence
<220> FEATURE:
<223> OTHER INFORMATION: Cleavage site, 2A-like sequence

<400> SEQUENCE: 23

Ala Ala Arg Gln Met Leu Leu Leu Leu Ser Gly Asp Val Glu Thr Asn
1               5                   10                  15

Pro Gly Pro

<210> SEQ ID NO 24
<211> LENGTH: 20
<212> TYPE: PRT
<213> ORGANISM: Artificial Sequence
<220> FEATURE:
<223> OTHER INFORMATION: Cleavage site, 2A-like sequence

<400> SEQUENCE: 24

Arg Ala Glu Gly Arg Gly Ser Leu Leu Thr Cys Gly Asp Val Glu Glu
1               5                   10                  15

Asn Pro Gly Pro
            20

<210> SEQ ID NO 25
<211> LENGTH: 20
<212> TYPE: PRT
<213> ORGANISM: Artificial Sequence
<220> FEATURE:
<223> OTHER INFORMATION: Cleavage site, 2A-like sequence

<400> SEQUENCE: 25

Thr Arg Ala Glu Ile Glu Asp Glu Leu Ile Arg Ala Gly Ile Glu Ser
1               5                   10                  15

Asn Pro Gly Pro
            20

<210> SEQ ID NO 26
<211> LENGTH: 20
<212> TYPE: PRT
<213> ORGANISM: Artificial Sequence
<220> FEATURE:
<223> OTHER INFORMATION: Cleavage site, 2A-like sequence

<400> SEQUENCE: 26

Thr Arg Ala Glu Ile Glu Asp Glu Leu Ile Arg Ala Asp Ile Glu Ser
1               5                   10                  15

Asn Pro Gly Pro
            20

<210> SEQ ID NO 27
<211> LENGTH: 20
<212> TYPE: PRT
<213> ORGANISM: Artificial Sequence
<220> FEATURE:
<223> OTHER INFORMATION: Cleavage site, 2A-like sequence

<400> SEQUENCE: 27

Ala Lys Phe Gln Ile Asp Lys Ile Leu Ile Ser Gly Asp Val Glu Leu
1               5                   10                  15

Asn Pro Gly Pro
            20
```

-continued

```
<210> SEQ ID NO 28
<211> LENGTH: 20
<212> TYPE: PRT
<213> ORGANISM: Artificial Sequence
<220> FEATURE:
<223> OTHER INFORMATION: Cleavage site, 2A-like sequence

<400> SEQUENCE: 28

Ser Ser Ile Ile Arg Thr Lys Met Leu Val Ser Gly Asp Val Glu Glu
1               5                   10                  15

Asn Pro Gly Pro
            20

<210> SEQ ID NO 29
<211> LENGTH: 20
<212> TYPE: PRT
<213> ORGANISM: Artificial Sequence
<220> FEATURE:
<223> OTHER INFORMATION: Cleavage site, 2A-like sequence

<400> SEQUENCE: 29

Cys Asp Ala Gln Arg Gln Lys Leu Leu Leu Ser Gly Asp Ile Glu Gln
1               5                   10                  15

Asn Pro Gly Pro
            20

<210> SEQ ID NO 30
<211> LENGTH: 20
<212> TYPE: PRT
<213> ORGANISM: Artificial Sequence
<220> FEATURE:
<223> OTHER INFORMATION: Cleavage site, 2A-like sequence

<400> SEQUENCE: 30

Tyr Pro Ile Asp Phe Gly Gly Phe Leu Val Lys Ala Asp Ser Glu Phe
1               5                   10                  15

Asn Pro Gly Pro
            20

<210> SEQ ID NO 31
<211> LENGTH: 57
<212> TYPE: PRT
<213> ORGANISM: Artificial Sequence
<220> FEATURE:
<223> OTHER INFORMATION: Cleavage sequence

<400> SEQUENCE: 31

Val Thr Glu Leu Leu Tyr Arg Met Lys Arg Ala Glu Thr Tyr Cys Pro
1               5                   10                  15

Arg Pro Leu Ala Ile His Pro Thr Glu Ala Arg His Lys Gln Lys Ile
            20                  25                  30

Val Ala Pro Val Lys Gln Thr Leu Asn Phe Asp Leu Leu Lys Leu Ala
        35                  40                  45

Gly Asp Val Glu Ser Asn Pro Gly Pro
    50                  55

<210> SEQ ID NO 32
<211> LENGTH: 40
<212> TYPE: PRT
<213> ORGANISM: Artificial Sequence
<220> FEATURE:
<223> OTHER INFORMATION: Cleavage sequence

<400> SEQUENCE: 32
```

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30

Asp Val Glu Ser Asn Pro Gly Pro
            35                  40

<210> SEQ ID NO 33
<211> LENGTH: 33
<212> TYPE: PRT
<213> ORGANISM: Artificial Sequence
<220> FEATURE:
<223> OTHER INFORMATION: Cleavage sequence

<400> SEQUENCE: 33

Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
            20                  25                  30

Pro

<210> SEQ ID NO 34
<211> LENGTH: 24
<212> TYPE: PRT
<213> ORGANISM: Artificial Sequence
<220> FEATURE:
<223> OTHER INFORMATION: Cleavage sequence

<400> SEQUENCE: 34

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 35
<211> LENGTH: 7
<212> TYPE: PRT
<213> ORGANISM: Artificial Sequence
<220> FEATURE:
<223> OTHER INFORMATION: Intracellular retention signal

<400> SEQUENCE: 35

Asn Gln Pro Leu Leu Thr Asp
1               5

<210> SEQ ID NO 36
<211> LENGTH: 15
<212> TYPE: PRT
<213> ORGANISM: Artificial Sequence
<220> FEATURE:
<223> OTHER INFORMATION: Intracellular retention signal

<400> SEQUENCE: 36

Lys Tyr Lys Ser Arg Arg Ser Phe Ile Asp Glu Lys Lys Met Pro
1               5                   10                  15

<210> SEQ ID NO 37
<211> LENGTH: 6
<212> TYPE: PRT
<213> ORGANISM: Artificial Sequence
<220> FEATURE:
<223> OTHER INFORMATION: Intracellular retention signal

<400> SEQUENCE: 37

Asp Glu Lys Lys Met Pro
1               5

<210> SEQ ID NO 38
<211> LENGTH: 21
<212> TYPE: PRT
<213> ORGANISM: Artificial Sequence
<220> FEATURE:
<223> OTHER INFORMATION: Signal peptide derived from Human CD8a

<400> SEQUENCE: 38

Met Ser Leu Pro Val Thr Ala Leu Leu Leu Pro Leu Ala Leu Leu Leu
1               5                   10                  15

His Ala Ala Arg Pro
            20

<210> SEQ ID NO 39
<211> LENGTH: 248
<212> TYPE: PRT
<213> ORGANISM: Artificial Sequence
<220> FEATURE:
<223> OTHER INFORMATION: scFv aCD19

<400> SEQUENCE: 39

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Lys Ala Gly Gly Gly
            100                 105                 110

Gly Ser Gly Gly Gly Gly Ser Gly Gly Gly Ser Gly Gly Gly Gly
        115                 120                 125

Ser Glu Val Lys Leu Gln Glu Ser Gly Pro Gly Leu Val Ala Pro Ser
    130                 135                 140

Gln Ser Leu Ser Val Thr Cys Thr Val Ser Gly Val Ser Leu Pro Asp
145                 150                 155                 160

Tyr Gly Val Ser Trp Ile Arg Gln Pro Pro Arg Lys Gly Leu Glu Trp
                165                 170                 175

Leu Gly Val Ile Trp Gly Ser Glu Thr Thr Tyr Tyr Asn Ser Ala Leu
            180                 185                 190

Lys Ser Arg Leu Thr Ile Ile Lys Asp Asn Ser Lys Ser Gln Val Phe
        195                 200                 205

Leu Lys Met Asn Ser Leu Gln Thr Asp Asp Thr Ala Ile Tyr Tyr Cys
    210                 215                 220

Ala Lys His Tyr Tyr Tyr Gly Gly Ser Tyr Ala Met Asp Tyr Trp Gly
225                 230                 235                 240

Gln Gly Thr Ser Val Thr Val Ser
                245

<210> SEQ ID NO 40

-continued

```
<211> LENGTH: 47
<212> TYPE: PRT
<213> ORGANISM: Artificial Sequence
<220> FEATURE:
<223> OTHER INFORMATION: Human CD8aSTK

<400> SEQUENCE: 40

Pro Thr Thr Thr Pro Ala Pro Arg Pro Pro Thr Pro Ala Pro Thr Ile
1               5                   10                  15

Ala Ser Gln Pro Leu Ser Leu Arg Pro Glu Ala Cys Arg Pro Ala Ala
            20                  25                  30

Gly Gly Ala Val His Thr Arg Gly Leu Asp Phe Ala Cys Asp Ile
        35                  40                  45

<210> SEQ ID NO 41
<211> LENGTH: 27
<212> TYPE: PRT
<213> ORGANISM: Artificial Sequence
<220> FEATURE:
<223> OTHER INFORMATION: Human CD28TM

<400> SEQUENCE: 41

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 42
<211> LENGTH: 36
<212> TYPE: PRT
<213> ORGANISM: Artificial Sequence
<220> FEATURE:
<223> OTHER INFORMATION: Human Typr-1 intracellular domain (retention
      signal)

<400> SEQUENCE: 42

Arg Ala Arg Arg Ser Met Asp Glu Ala Asn Gln Pro Leu Leu Thr Asp
1               5                   10                  15

Gln Tyr Gln Cys Tyr Ala Glu Glu Tyr Glu Lys Leu Gln Asn Pro Asn
            20                  25                  30

Gln Ser Val Val
        35

<210> SEQ ID NO 43
<211> LENGTH: 113
<212> TYPE: PRT
<213> ORGANISM: Artificial Sequence
<220> FEATURE:
<223> OTHER INFORMATION: Human CD3zeta intracellular domain

<400> SEQUENCE: 43

Arg Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Arg Gly Arg Asp Pro Glu Met Gly Gly
        35                  40                  45

Lys Pro Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
```

```
            85                  90                  95
Ala Thr Lys Asp Thr Tyr Asp Ala Leu His Met Gln Ala Leu Pro Pro
            100                 105                 110
Arg
```

<210> SEQ ID NO 44
<211> LENGTH: 18
<212> TYPE: PRT
<213> ORGANISM: Artificial Sequence
<220> FEATURE:
<223> OTHER INFORMATION: Signal peptide derived from mouse Ig kappa

<400> SEQUENCE: 44

```
Met Ala Val Pro Thr Gln Val Leu Gly Leu Leu Leu Leu Trp Leu Thr
1               5                   10                  15
Asp Ala
```

<210> SEQ ID NO 45
<211> LENGTH: 254
<212> TYPE: PRT
<213> ORGANISM: Artificial Sequence
<220> FEATURE:
<223> OTHER INFORMATION: scFv aCD33

<400> SEQUENCE: 45

```
Arg Cys Asp Ile Gln Met Thr Gln Ser Pro Ser Ser Leu Ser Ala Ser
1               5                   10                  15

Val Gly Asp Arg Val Thr Ile Thr Cys Arg Ala Ser Glu Asp Ile Tyr
            20                  25                  30

Phe Asn Leu Val Trp Tyr Gln Gln Lys Pro Gly Lys Ala Pro Lys Leu
        35                  40                  45

Leu Ile Tyr Asp Thr Asn Arg Leu Ala Asp Gly Val Pro Ser Arg Phe
    50                  55                  60

Ser Gly Ser Gly Ser Gly Thr Gln Tyr Thr Leu Thr Ile Ser Ser Leu
65                  70                  75                  80

Gln Pro Glu Asp Phe Ala Thr Tyr Tyr Cys Gln His Tyr Lys Asn Tyr
                85                  90                  95

Pro Leu Thr Phe Gly Gln Gly Thr Lys Leu Glu Ile Lys Arg Ser Gly
            100                 105                 110

Gly Gly Gly Ser Gly Gly Gly Ser Gly Gly Gly Ser Gly Gly
            115                 120                 125

Gly Gly Ser Arg Ser Glu Val Gln Leu Val Glu Ser Gly Gly Gly Leu
        130                 135                 140

Val Gln Pro Gly Gly Ser Leu Arg Leu Ser Cys Ala Ala Ser Gly Phe
145                 150                 155                 160

Thr Leu Ser Asn Tyr Gly Met His Trp Ile Arg Gln Ala Pro Gly Lys
                165                 170                 175

Gly Leu Glu Trp Val Ser Ser Ile Ser Leu Asn Gly Gly Ser Thr Tyr
            180                 185                 190

Tyr Arg Asp Ser Val Lys Gly Arg Phe Thr Ile Ser Arg Asp Asn Ala
        195                 200                 205

Lys Ser Thr Leu Tyr Leu Gln Met Asn Ser Leu Arg Ala Glu Asp Thr
    210                 215                 220

Ala Val Tyr Tyr Cys Ala Ala Gln Asp Ala Tyr Thr Gly Gly Tyr Phe
225                 230                 235                 240

Asp Tyr Trp Gly Gln Gly Thr Leu Val Thr Val Ser Ser Met
                245                 250
```

<210> SEQ ID NO 46
<211> LENGTH: 231
<212> TYPE: PRT
<213> ORGANISM: Artificial Sequence
<220> FEATURE:
<223> OTHER INFORMATION: Hinge and Fc derived from human IgG1 with
      mutations to prevent FcRg association (HCH2CH3pvaa)

<400> SEQUENCE: 46

```
Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Lys Pro Lys
            20                  25                  30

Asp Thr Leu Met Ile Ala Arg Thr Pro Glu Val Thr Cys Val Val Val
            35                  40                  45

Asp Val Ser His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
210                 215                 220

Leu Ser Leu Ser Pro Gly Lys
225                 230
```

<210> SEQ ID NO 47
<211> LENGTH: 4
<212> TYPE: PRT
<213> ORGANISM: Artificial Sequence
<220> FEATURE:
<223> OTHER INFORMATION: Linker

<400> SEQUENCE: 47

```
Lys Asp Pro Lys
1
```

<210> SEQ ID NO 48
<211> LENGTH: 21
<212> TYPE: PRT
<213> ORGANISM: Artificial Sequence
<220> FEATURE:
<223> OTHER INFORMATION: Human CD148TM

<400> SEQUENCE: 48

Ala Val Phe Gly Cys Ile Phe Gly Ala Leu Val Ile Val Thr Val Gly
1               5                   10                  15

Gly Phe Ile Phe Trp
            20

<210> SEQ ID NO 49
<211> LENGTH: 341
<212> TYPE: PRT
<213> ORGANISM: Artificial Sequence
<220> FEATURE:
<223> OTHER INFORMATION: Human CD148 intracellular domain

<400> SEQUENCE: 49

Arg Lys Lys Arg Lys Asp Ala Lys Asn Asn Glu Val Ser Phe Ser Gln
1               5                   10                  15

Ile Lys Pro Lys Lys Ser Lys Leu Ile Arg Val Glu Asn Phe Glu Ala
            20                  25                  30

Tyr Phe Lys Lys Gln Gln Ala Asp Ser Asn Cys Gly Phe Ala Glu Glu
        35                  40                  45

Tyr Glu Asp Leu Lys Leu Val Gly Ile Ser Gln Pro Lys Tyr Ala Ala
    50                  55                  60

Glu Leu Ala Glu Asn Arg Gly Lys Asn Arg Tyr Asn Asn Val Leu Pro
65                  70                  75                  80

Tyr Asp Ile Ser Arg Val Lys Leu Ser Val Gln Thr His Ser Thr Asp
                85                  90                  95

Asp Tyr Ile Asn Ala Asn Tyr Met Pro Gly Tyr His Ser Lys Lys Asp
            100                 105                 110

Phe Ile Ala Thr Gln Gly Pro Leu Pro Asn Thr Leu Lys Asp Phe Trp
        115                 120                 125

Arg Met Val Trp Glu Lys Asn Val Tyr Ala Ile Ile Met Leu Thr Lys
    130                 135                 140

Cys Val Glu Gln Gly Arg Thr Lys Cys Glu Glu Tyr Trp Pro Ser Lys
145                 150                 155                 160

Gln Ala Gln Asp Tyr Gly Asp Ile Thr Val Ala Met Thr Ser Glu Ile
                165                 170                 175

Val Leu Pro Glu Trp Thr Ile Arg Asp Phe Thr Val Lys Asn Ile Gln
            180                 185                 190

Thr Ser Glu Ser His Pro Leu Arg Gln Phe His Phe Thr Ser Trp Pro
        195                 200                 205

Asp His Gly Val Pro Asp Thr Thr Asp Leu Leu Ile Asn Phe Arg Tyr
    210                 215                 220

Leu Val Arg Asp Tyr Met Lys Gln Ser Pro Pro Glu Ser Pro Ile Leu
225                 230                 235                 240

Val His Cys Ser Ala Gly Val Gly Arg Thr Gly Thr Phe Ile Ala Ile
                245                 250                 255

Asp Arg Leu Ile Tyr Gln Ile Glu Asn Glu Asn Thr Val Asp Val Tyr
            260                 265                 270

Gly Ile Val Tyr Asp Leu Arg Met His Arg Pro Leu Met Val Gln Thr
        275                 280                 285

Glu Asp Gln Tyr Val Phe Leu Asn Gln Cys Val Leu Asp Ile Val Arg
    290                 295                 300

Ser Gln Lys Asp Ser Lys Val Asp Leu Ile Tyr Gln Asn Thr Thr Ala
305                 310                 315                 320

Met Thr Ile Tyr Glu Asn Leu Ala Pro Val Thr Thr Phe Gly Lys Thr
                325                 330                 335

Asn Gly Tyr Ile Ala
            340

<210> SEQ ID NO 50
<211> LENGTH: 4
<212> TYPE: PRT
<213> ORGANISM: Artificial Sequence
<220> FEATURE:
<223> OTHER INFORMATION: Intracellular retention signal
<220> FEATURE:
<221> NAME/KEY: misc_feature
<222> LOCATION: (4)..(4)
<223> OTHER INFORMATION: Xaa can be any naturally occurring amino acid

<400> SEQUENCE: 50

Asn Pro Phe Xaa
1

<210> SEQ ID NO 51
<211> LENGTH: 4
<212> TYPE: PRT
<213> ORGANISM: Artificial Sequence
<220> FEATURE:
<223> OTHER INFORMATION: Intracellular retention signal

<400> SEQUENCE: 51

Lys Asp Glu Leu
1

<210> SEQ ID NO 52
<211> LENGTH: 4
<212> TYPE: PRT
<213> ORGANISM: Artificial Sequence
<220> FEATURE:
<223> OTHER INFORMATION: Intracellular retention signal
<220> FEATURE:
<221> NAME/KEY: misc_feature
<222> LOCATION: (3)..(4)
<223> OTHER INFORMATION: Xaa can be any naturally occurring amino acid

<400> SEQUENCE: 52

Lys Lys Xaa Xaa
1

<210> SEQ ID NO 53
<211> LENGTH: 5
<212> TYPE: PRT
<213> ORGANISM: Artificial Sequence
<220> FEATURE:
<223> OTHER INFORMATION: Intracellular retention signal
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 53

Lys Xaa Lys Xaa Xaa
1               5

<210> SEQ ID NO 54
<211> LENGTH: 4
<212> TYPE: PRT
<213> ORGANISM: Artificial Sequence
<220> FEATURE:
<223> OTHER INFORMATION: Intracellular retention signal

```
<220> FEATURE:
<221> NAME/KEY: misc_feature
<222> LOCATION: (3)..(3)
<223> OTHER INFORMATION: Xaa can be any naturally occurring amino acid

<400> SEQUENCE: 54

Asn Pro Xaa Tyr
1

<210> SEQ ID NO 55
<211> LENGTH: 4
<212> TYPE: PRT
<213> ORGANISM: Artificial Sequence
<220> FEATURE:
<223> OTHER INFORMATION: Intracellular retention signal
<220> FEATURE:
<221> NAME/KEY: MISC_FEATURE
<222> LOCATION: (2)..(2)
<223> OTHER INFORMATION: Xaa can be any naturally occuring amino acid.
<220> FEATURE:
<221> NAME/KEY: MISC_FEATURE
<222> LOCATION: (3)..(3)
<223> OTHER INFORMATION: Xaa can be any naturally occurring amino acid.
<220> FEATURE:
<221> NAME/KEY: MISC_FEATURE
<222> LOCATION: (4)..(4)
<223> OTHER INFORMATION: Xaa is an amino acid with a bulky hydrophobic
      side chain.

<400> SEQUENCE: 55

Tyr Xaa Xaa Xaa
1

<210> SEQ ID NO 56
<211> LENGTH: 8
<212> TYPE: PRT
<213> ORGANISM: Artificial Sequence
<220> FEATURE:
<223> OTHER INFORMATION: Intracellular retention signal
<220> FEATURE:
<221> NAME/KEY: misc_feature
<222> LOCATION: (3)..(5)
<223> OTHER INFORMATION: Xaa can be any naturally occurring amino acid

<400> SEQUENCE: 56

Asp Glu Xaa Xaa Xaa Leu Leu Ile
1               5

<210> SEQ ID NO 57
<211> LENGTH: 5
<212> TYPE: PRT
<213> ORGANISM: Artificial Sequence
<220> FEATURE:
<223> OTHER INFORMATION: Intracellular retention signal
<220> FEATURE:
<221> NAME/KEY: misc_feature
<222> LOCATION: (2)..(3)
<223> OTHER INFORMATION: Xaa can be any naturally occurring amino acid

<400> SEQUENCE: 57

Asp Xaa Xaa Leu Leu
1               5

<210> SEQ ID NO 58
<211> LENGTH: 4
<212> TYPE: PRT
<213> ORGANISM: Artificial Sequence
<220> FEATURE:
<223> OTHER INFORMATION: Intracellular retention signal

<400> SEQUENCE: 58
```

Asp Pro Phe Trp
1

<210> SEQ ID NO 59
<211> LENGTH: 5
<212> TYPE: PRT
<213> ORGANISM: Artificial Sequence
<220> FEATURE:
<223> OTHER INFORMATION: Intracellular retention signal
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 59

Phe Xaa Asp Xaa Phe
1               5

<210> SEQ ID NO 60
<211> LENGTH: 6
<212> TYPE: PRT
<213> ORGANISM: Artificial Sequence
<220> FEATURE:
<223> OTHER INFORMATION: Intracellular retention signal
<220> FEATURE:
<221> NAME/KEY: MISC_FEATURE
<222> LOCATION: (2)..(2)
<223> OTHER INFORMATION: Xaa is an amino acid with a bulky hydrophobic
      side chain.
<220> FEATURE:
<221> NAME/KEY: MISC_FEATURE
<222> LOCATION: (3)..(3)
<223> OTHER INFORMATION: Xaa can be any naturally occuring amino acid.
<220> FEATURE:
<221> NAME/KEY: MISC_FEATURE
<222> LOCATION: (4)..(4)
<223> OTHER INFORMATION: Xaa is an amino acid with a bulky hydrophobic
      side chain.

<400> SEQUENCE: 60

Leu Xaa Xaa Xaa Asp Glu
1               5

<210> SEQ ID NO 61
<211> LENGTH: 5
<212> TYPE: PRT
<213> ORGANISM: Artificial Sequence
<220> FEATURE:
<223> OTHER INFORMATION: Intracellular retention signal

<400> SEQUENCE: 61

Leu Leu Asp Leu Leu
1               5

<210> SEQ ID NO 62
<211> LENGTH: 5
<212> TYPE: PRT
<213> ORGANISM: Artificial Sequence
<220> FEATURE:
<223> OTHER INFORMATION: Intracellular retention signal

<400> SEQUENCE: 62

Pro Trp Asp Leu Trp
1               5

```
<210> SEQ ID NO 63
<211> LENGTH: 4
<212> TYPE: PRT
<213> ORGANISM: Artificial Sequence
<220> FEATURE:
<223> OTHER INFORMATION: Furin cleavage site
<220> FEATURE:
<221> NAME/KEY: MISC_FEATURE
<222> LOCATION: (2)..(2)
<223> OTHER INFORMATION: Xaa can be any naturally occuring amino acid.
<220> FEATURE:
<221> NAME/KEY: MISC_FEATURE
<222> LOCATION: (3)..(3)
<223> OTHER INFORMATION: Xaa can be ARG or LYS

<400> SEQUENCE: 63

Arg Xaa Xaa Arg
1

<210> SEQ ID NO 64
<211> LENGTH: 7
<212> TYPE: PRT
<213> ORGANISM: Artificial Sequence
<220> FEATURE:
<223> OTHER INFORMATION: Tobacco Etch Virus (TEV) cleavage site

<400> SEQUENCE: 64

Glu Asn Leu Tyr Phe Gln Ser
1               5

<210> SEQ ID NO 65
<211> LENGTH: 8
<212> TYPE: PRT
<213> ORGANISM: Artificial Sequence
<220> FEATURE:
<223> OTHER INFORMATION: Cleavage site
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 65

Asp Xaa Glu Xaa Asn Pro Gly Pro
1               5

<210> SEQ ID NO 66
<211> LENGTH: 8
<212> TYPE: PRT
<213> ORGANISM: Artificial Sequence
<220> FEATURE:
<223> OTHER INFORMATION: Cleavage site
<220> FEATURE:
<221> NAME/KEY: MISC_FEATURE
<222> LOCATION: (2)..(2)
<223> OTHER INFORMATION: Xaa may be selected from the following group:
      ILE, VAL, MET and SER
<220> FEATURE:
<221> NAME/KEY: MISC_FEATURE
<222> LOCATION: (4)..(4)
<223> OTHER INFORMATION: Xaa may be selected from the following group:
      THR, MET, SER, LEU, GLU, GLN and PHE.

<400> SEQUENCE: 66

Asp Xaa Glu Xaa Asn Pro Gly Pro
1               5

<210> SEQ ID NO 67
```

```
<211> LENGTH: 4
<212> TYPE: PRT
<213> ORGANISM: Artificial Sequence
<220> FEATURE:
<223> OTHER INFORMATION: Endoplasmic reticulum (ER) retention signal
<220> FEATURE:
<221> NAME/KEY: misc_feature
<222> LOCATION: (2)..(2)
<223> OTHER INFORMATION: Xaa can be any naturally occurring amino acid

<400> SEQUENCE: 67

Arg Xaa Arg Arg
1

<210> SEQ ID NO 68
<211> LENGTH: 12
<212> TYPE: PRT
<213> ORGANISM: Homo sapiens

<400> SEQUENCE: 68

Ile Asn Phe Asp Asn Pro Val Tyr Gln Lys Thr Thr
1               5                   10

<210> SEQ ID NO 69
<211> LENGTH: 12
<212> TYPE: PRT
<213> ORGANISM: Homo sapiens

<400> SEQUENCE: 69

Val Glu Ile Gly Asn Pro Thr Tyr Lys Met Tyr Glu
1               5                   10

<210> SEQ ID NO 70
<211> LENGTH: 12
<212> TYPE: PRT
<213> ORGANISM: Homo sapiens

<400> SEQUENCE: 70

Thr Asn Phe Thr Asn Pro Val Tyr Ala Thr Leu Tyr
1               5                   10

<210> SEQ ID NO 71
<211> LENGTH: 12
<212> TYPE: PRT
<213> ORGANISM: Drosophila sp.

<400> SEQUENCE: 71

Gly Asn Phe Ala Asn Pro Val Tyr Glu Ser Met Tyr
1               5                   10

<210> SEQ ID NO 72
<211> LENGTH: 12
<212> TYPE: PRT
<213> ORGANISM: Caenorhabditis elegans

<400> SEQUENCE: 72

Thr Thr Phe Thr Asn Pro Val Tyr Glu Leu Glu Asp
1               5                   10

<210> SEQ ID NO 73
<211> LENGTH: 12
<212> TYPE: PRT
<213> ORGANISM: Caenorhabditis elegans

<400> SEQUENCE: 73

Leu Arg Val Asp Asn Pro Leu Tyr Asp Pro Asp Ser
```

-continued

```
<210> SEQ ID NO 74
<211> LENGTH: 12
<212> TYPE: PRT
<213> ORGANISM: Homo sapiens

<400> SEQUENCE: 74

Ile Ile Phe Glu Asn Pro Met Tyr Ser Ala Arg Asp
1               5                   10

<210> SEQ ID NO 75
<211> LENGTH: 12
<212> TYPE: PRT
<213> ORGANISM: Homo sapiens

<400> SEQUENCE: 75

Thr Asn Phe Glu Asn Pro Ile Tyr Ala Gln Met Glu
1               5                   10

<210> SEQ ID NO 76
<211> LENGTH: 12
<212> TYPE: PRT
<213> ORGANISM: Homo sapiens

<400> SEQUENCE: 76

Asp Thr Gly Glu Asn Pro Ile Tyr Lys Ser Ala Val
1               5                   10

<210> SEQ ID NO 77
<211> LENGTH: 11
<212> TYPE: PRT
<213> ORGANISM: Homo sapiens

<400> SEQUENCE: 77

Thr Thr Val Val Asn Pro Lys Tyr Glu Gly Lys
1               5                   10

<210> SEQ ID NO 78
<211> LENGTH: 12
<212> TYPE: PRT
<213> ORGANISM: Drosophila sp.

<400> SEQUENCE: 78

Trp Asp Thr Glu Asn Pro Ile Tyr Lys Gln Ala Thr
1               5                   10

<210> SEQ ID NO 79
<211> LENGTH: 11
<212> TYPE: PRT
<213> ORGANISM: Drosophila sp.

<400> SEQUENCE: 79

Ser Thr Phe Lys Asn Pro Met Tyr Ala Gly Lys
1               5                   10

<210> SEQ ID NO 80
<211> LENGTH: 12
<212> TYPE: PRT
<213> ORGANISM: Homo sapiens

<400> SEQUENCE: 80

His Gly Tyr Glu Asn Pro Thr Tyr Arg Phe Leu Glu
1               5                   10
```

<210> SEQ ID NO 81
<211> LENGTH: 12
<212> TYPE: PRT
<213> ORGANISM: Homo sapiens

<400> SEQUENCE: 81

Asn Gly Tyr Glu Asn Pro Thr Tyr Lys Phe Phe Glu
1               5                   10

<210> SEQ ID NO 82
<211> LENGTH: 12
<212> TYPE: PRT
<213> ORGANISM: Drosophila sp.

<400> SEQUENCE: 82

Asn Gly Tyr Glu Asn Pro Thr Tyr Lys Tyr Phe Glu
1               5                   10

<210> SEQ ID NO 83
<211> LENGTH: 12
<212> TYPE: PRT
<213> ORGANISM: Homo sapiens

<400> SEQUENCE: 83

Tyr Ala Ser Ser Asn Pro Glu Tyr Leu Ser Ala Ser
1               5                   10

<210> SEQ ID NO 84
<211> LENGTH: 12
<212> TYPE: PRT
<213> ORGANISM: Homo sapiens

<400> SEQUENCE: 84

Gly Ser Val Gln Asn Pro Val Tyr His Asn Gln Pro
1               5                   10

<210> SEQ ID NO 85
<211> LENGTH: 12
<212> TYPE: PRT
<213> ORGANISM: Homo sapiens

<400> SEQUENCE: 85

Thr Ala Val Gly Asn Pro Glu Tyr Leu Asn Thr Val
1               5                   10

<210> SEQ ID NO 86
<211> LENGTH: 12
<212> TYPE: PRT
<213> ORGANISM: Homo sapiens

<400> SEQUENCE: 86

Ile Ser Leu Asp Asn Pro Asp Tyr Gln Gln Asp Phe
1               5                   10

<210> SEQ ID NO 87
<211> LENGTH: 11
<212> TYPE: PRT
<213> ORGANISM: Homo sapiens

<400> SEQUENCE: 87

Arg Lys Arg Ser His Ala Gly Tyr Gln Thr Ile
1               5                   10

<210> SEQ ID NO 88

<210> SEQ ID NO 88
<211> LENGTH: 10
<212> TYPE: PRT
<213> ORGANISM: Homo sapiens

<400> SEQUENCE: 88

Lys His His His Ala Gly Tyr Glu Gln Phe
1               5                   10

<210> SEQ ID NO 89
<211> LENGTH: 11
<212> TYPE: PRT
<213> ORGANISM: Gallus gallus

<400> SEQUENCE: 89

Lys Lys His His Asn Thr Gly Tyr Glu Gln Phe
1               5                   10

<210> SEQ ID NO 90
<211> LENGTH: 11
<212> TYPE: PRT
<213> ORGANISM: Gallus gallus

<400> SEQUENCE: 90

Arg Arg Lys Ser Arg Thr Gly Tyr Gln Ser Val
1               5                   10

<210> SEQ ID NO 91
<211> LENGTH: 11
<212> TYPE: PRT
<213> ORGANISM: Gallus gallus

<400> SEQUENCE: 91

Arg Arg Lys Ser Tyr Ala Gly Tyr Gln Thr Leu
1               5                   10

<210> SEQ ID NO 92
<211> LENGTH: 12
<212> TYPE: PRT
<213> ORGANISM: Drosophila sp.

<400> SEQUENCE: 92

Arg Arg Arg Ser Thr Ser Arg Gly Tyr Met Ser Phe
1               5                   10

<210> SEQ ID NO 93
<211> LENGTH: 11
<212> TYPE: PRT
<213> ORGANISM: Lumbricus terrestris

<400> SEQUENCE: 93

Arg Lys Arg Ser Arg Arg Gly Tyr Glu Ser Val
1               5                   10

<210> SEQ ID NO 94
<211> LENGTH: 10
<212> TYPE: PRT
<213> ORGANISM: Homo sapiens

<400> SEQUENCE: 94

Lys Ser Ile Arg Ser Gly Tyr Glu Val Met
1               5                   10

<210> SEQ ID NO 95
<211> LENGTH: 12
<212> TYPE: PRT

<213> ORGANISM: Homo sapiens

<400> SEQUENCE: 95

His Cys Gly Gly Pro Arg Pro Gly Tyr Glu Thr Leu
1               5                   10

<210> SEQ ID NO 96
<211> LENGTH: 12
<212> TYPE: PRT
<213> ORGANISM: Mus musculus

<400> SEQUENCE: 96

His Cys Arg Thr Arg Arg Ala Glu Tyr Glu Thr Leu
1               5                   10

<210> SEQ ID NO 97
<211> LENGTH: 10
<212> TYPE: PRT
<213> ORGANISM: Homo sapiens

<400> SEQUENCE: 97

Arg Arg Arg Pro Ser Ala Tyr Gln Ala Leu
1               5                   10

<210> SEQ ID NO 98
<211> LENGTH: 9
<212> TYPE: PRT
<213> ORGANISM: Homo sapiens

<400> SEQUENCE: 98

Arg Arg Arg Ser Tyr Gln Asn Ile Pro
1               5

<210> SEQ ID NO 99
<211> LENGTH: 10
<212> TYPE: PRT
<213> ORGANISM: Homo sapiens

<400> SEQUENCE: 99

Lys Lys His Cys Ser Tyr Gln Asp Ile Leu
1               5                   10

<210> SEQ ID NO 100
<211> LENGTH: 10
<212> TYPE: PRT
<213> ORGANISM: Mus musculus

<400> SEQUENCE: 100

Arg Arg Arg Ser Ala Tyr Gln Asp Ile Arg
1               5                   10

<210> SEQ ID NO 101
<211> LENGTH: 11
<212> TYPE: PRT
<213> ORGANISM: Rattus norvegicus

<400> SEQUENCE: 101

Arg Lys Arg Arg Arg Ser Tyr Gln Asp Ile Met
1               5                   10

<210> SEQ ID NO 102
<211> LENGTH: 13
<212> TYPE: PRT
<213> ORGANISM: Rattus norvegicus

<400> SEQUENCE: 102

Lys Phe Cys Lys Ser Lys Glu Arg Asn Tyr His Thr Leu
1               5                   10

<210> SEQ ID NO 103
<211> LENGTH: 14
<212> TYPE: PRT
<213> ORGANISM: Drosophila sp.

<400> SEQUENCE: 103

Lys Phe Tyr Lys Ala Arg Asn Glu Arg Asn Tyr His Thr Leu
1               5                   10

<210> SEQ ID NO 104
<211> LENGTH: 14
<212> TYPE: PRT
<213> ORGANISM: Homo sapiens

<400> SEQUENCE: 104

Lys Ile Arg Leu Arg Cys Gln Ser Ser Gly Tyr Gln Arg Ile
1               5                   10

<210> SEQ ID NO 105
<211> LENGTH: 14
<212> TYPE: PRT
<213> ORGANISM: Mus musculus

<400> SEQUENCE: 105

Lys Ile Arg Gln Arg His Gln Ser Ser Ala Tyr Gln Arg Ile
1               5                   10

<210> SEQ ID NO 106
<211> LENGTH: 15
<212> TYPE: PRT
<213> ORGANISM: Homo sapiens

<400> SEQUENCE: 106

His Phe Cys Leu Tyr Arg Lys Arg Pro Gly Tyr Asp Gln Leu Asn
1               5                   10                  15

<210> SEQ ID NO 107
<211> LENGTH: 11
<212> TYPE: PRT
<213> ORGANISM: Homo sapiens

<400> SEQUENCE: 107

Ser Leu Ser Arg Gly Ser Gly Tyr Lys Glu Ile
1               5                   10

<210> SEQ ID NO 108
<211> LENGTH: 13
<212> TYPE: PRT
<213> ORGANISM: Homo sapiens

<400> SEQUENCE: 108

Arg Arg Leu Arg Lys Gly Tyr Thr Pro Leu Met Glu Thr
1               5                   10

<210> SEQ ID NO 109
<211> LENGTH: 14
<212> TYPE: PRT
<213> ORGANISM: Homo sapiens

<400> SEQUENCE: 109

```
Arg Arg Ala Gly His Ser Ser Tyr Thr Pro Leu Pro Gly Ser
1               5                   10
```

<210> SEQ ID NO 110
<211> LENGTH: 18
<212> TYPE: PRT
<213> ORGANISM: Dictyostelium discoideum

<400> SEQUENCE: 110

```
Lys Lys Leu Arg Gln Gln Lys Gln Gln Gly Tyr Gln Ala Ile Ile Asn
1               5                   10                  15

Asn Glu
```

<210> SEQ ID NO 111
<211> LENGTH: 15
<212> TYPE: PRT
<213> ORGANISM: Dictyostelium discoideum

<400> SEQUENCE: 111

```
Arg Ser Lys Ser Asn Gln Asn Gln Ser Tyr Asn Leu Ile Gln Leu
1               5                   10                  15
```

<210> SEQ ID NO 112
<211> LENGTH: 17
<212> TYPE: PRT
<213> ORGANISM: Dictyostelium discoideum

<400> SEQUENCE: 112

```
Arg Lys Thr Phe Tyr Asn Asn Asn Gln Tyr Asn Gly Tyr Asn Ile Ile
1               5                   10                  15

Asn
```

<210> SEQ ID NO 113
<211> LENGTH: 10
<212> TYPE: PRT
<213> ORGANISM: Homo sapiens

<400> SEQUENCE: 113

```
Pro Leu Ser Tyr Thr Arg Phe Ser Leu Ala
1               5                   10
```

<210> SEQ ID NO 114
<211> LENGTH: 11
<212> TYPE: PRT
<213> ORGANISM: Homo sapiens

<400> SEQUENCE: 114

```
Met Thr Lys Glu Tyr Gln Asp Leu Gln His Leu
1               5                   10
```

<210> SEQ ID NO 115
<211> LENGTH: 10
<212> TYPE: PRT
<213> ORGANISM: Homo sapiens

<400> SEQUENCE: 115

```
Ser Tyr Lys Tyr Ser Lys Val Asn Lys Glu
1               5                   10
```

<210> SEQ ID NO 116
<211> LENGTH: 10
<212> TYPE: PRT
<213> ORGANISM: Homo sapiens

```
<400> SEQUENCE: 116

Pro Ala Ala Tyr Arg Gly Val Gly Asp Asp
1               5                   10

<210> SEQ ID NO 117
<211> LENGTH: 10
<212> TYPE: PRT
<213> ORGANISM: Homo sapiens

<400> SEQUENCE: 117

Thr Gly Val Tyr Val Lys Met Pro Pro Thr
1               5                   10

<210> SEQ ID NO 118
<211> LENGTH: 10
<212> TYPE: PRT
<213> ORGANISM: Homo sapiens

<400> SEQUENCE: 118

Leu Ile Ser Tyr Lys Gly Leu Pro Pro Glu
1               5                   10

<210> SEQ ID NO 119
<211> LENGTH: 11
<212> TYPE: PRT
<213> ORGANISM: Rattus norvegicus

<400> SEQUENCE: 119

Ala Ser Asp Tyr Gln Arg Leu Asn Leu Lys Leu
1               5                   10

<210> SEQ ID NO 120
<211> LENGTH: 11
<212> TYPE: PRT
<213> ORGANISM: Human immunodeficiency virus type 1

<400> SEQUENCE: 120

Arg Gln Gly Tyr Ser Pro Leu Ser Phe Gln Thr
1               5                   10

<210> SEQ ID NO 121
<211> LENGTH: 19
<212> TYPE: PRT
<213> ORGANISM: Homo sapiens

<400> SEQUENCE: 121

Arg Met Gln Ala Gln Pro Pro Gly Tyr Arg His Val Ala Asp Gly Glu
1               5                   10                  15

Asp His Ala

<210> SEQ ID NO 122
<211> LENGTH: 9
<212> TYPE: PRT
<213> ORGANISM: Artificial Sequence
<220> FEATURE:
<223> OTHER INFORMATION: Dileucine-based sorting signal
<220> FEATURE:
<221> NAME/KEY: misc_feature
<222> LOCATION: (3)..(5)
<223> OTHER INFORMATION: Xaa can be any naturally occurring amino acid

<400> SEQUENCE: 122

Asp Glu Xaa Xaa Xaa Leu Leu Leu Ile
1               5
```

<210> SEQ ID NO 123
<211> LENGTH: 9
<212> TYPE: PRT
<213> ORGANISM: Homo sapiens

<400> SEQUENCE: 123

Ser Asp Lys Gln Thr Leu Leu Pro Asn
1               5

<210> SEQ ID NO 124
<211> LENGTH: 9
<212> TYPE: PRT
<213> ORGANISM: Rattus norvegicus

<400> SEQUENCE: 124

Asp Glu Arg Ala Pro Leu Ile Arg Thr
1               5

<210> SEQ ID NO 125
<211> LENGTH: 9
<212> TYPE: PRT
<213> ORGANISM: Homo sapiens

<400> SEQUENCE: 125

Gln Glu Lys Asp Pro Leu Leu Lys Asn
1               5

<210> SEQ ID NO 126
<211> LENGTH: 9
<212> TYPE: PRT
<213> ORGANISM: Coturnix coturnix

<400> SEQUENCE: 126

Thr Glu Arg Asn Pro Leu Leu Lys Ser
1               5

<210> SEQ ID NO 127
<211> LENGTH: 9
<212> TYPE: PRT
<213> ORGANISM: Homo sapiens

<400> SEQUENCE: 127

Gly Glu Asn Ser Pro Leu Leu Ser Gly
1               5

<210> SEQ ID NO 128
<211> LENGTH: 9
<212> TYPE: PRT
<213> ORGANISM: Homo sapiens

<400> SEQUENCE: 128

Glu Glu Lys Gln Pro Leu Leu Met Glu
1               5

<210> SEQ ID NO 129
<211> LENGTH: 9
<212> TYPE: PRT
<213> ORGANISM: Oryzias latipes

<400> SEQUENCE: 129

Gly Glu Arg Gln Pro Leu Leu Gln Ser
1               5

<210> SEQ ID NO 130

```
<211> LENGTH: 9
<212> TYPE: PRT
<213> ORGANISM: Gallus gallus

<400> SEQUENCE: 130

Pro Glu Ile Gln Pro Leu Leu Thr Glu
1               5

<210> SEQ ID NO 131
<211> LENGTH: 9
<212> TYPE: PRT
<213> ORGANISM: Carassius auratus

<400> SEQUENCE: 131

Glu Gly Arg Gln Pro Leu Leu Gly Asp
1               5

<210> SEQ ID NO 132
<211> LENGTH: 9
<212> TYPE: PRT
<213> ORGANISM: Homo sapiens

<400> SEQUENCE: 132

Glu Ala Asn Gln Pro Leu Leu Thr Asp
1               5

<210> SEQ ID NO 133
<211> LENGTH: 9
<212> TYPE: PRT
<213> ORGANISM: Gallus gallus

<400> SEQUENCE: 133

Glu Leu His Gln Pro Leu Leu Thr Asp
1               5

<210> SEQ ID NO 134
<211> LENGTH: 9
<212> TYPE: PRT
<213> ORGANISM: Danio rerio

<400> SEQUENCE: 134

Arg Glu Phe Glu Pro Leu Leu Asn Ala
1               5

<210> SEQ ID NO 135
<211> LENGTH: 9
<212> TYPE: PRT
<213> ORGANISM: Homo sapiens

<400> SEQUENCE: 135

Glu Glu Lys Met Ala Ile Leu Met Asp
1               5

<210> SEQ ID NO 136
<211> LENGTH: 9
<212> TYPE: PRT
<213> ORGANISM: Homo sapiens

<400> SEQUENCE: 136

Glu Glu Lys Leu Ala Ile Leu Ser Gln
1               5

<210> SEQ ID NO 137
<211> LENGTH: 9
<212> TYPE: PRT
```

```
<213> ORGANISM: Mus musculus

<400> SEQUENCE: 137

Ser Glu Arg Asp Val Leu Leu Asp Glu
1               5

<210> SEQ ID NO 138
<211> LENGTH: 9
<212> TYPE: PRT
<213> ORGANISM: Homo sapiens

<400> SEQUENCE: 138

Ser Glu Arg Arg Asn Leu Leu Glu Asp
1               5

<210> SEQ ID NO 139
<211> LENGTH: 9
<212> TYPE: PRT
<213> ORGANISM: Rattus norvegicus

<400> SEQUENCE: 139

Asp Asp Ser Gly Asp Leu Leu Pro Gly
1               5

<210> SEQ ID NO 140
<211> LENGTH: 9
<212> TYPE: PRT
<213> ORGANISM: Homo sapiens

<400> SEQUENCE: 140

Ser Gln Ile Lys Arg Leu Leu Ser Glu
1               5

<210> SEQ ID NO 141
<211> LENGTH: 9
<212> TYPE: PRT
<213> ORGANISM: Felis catus

<400> SEQUENCE: 141

Ser His Ile Lys Arg Leu Leu Ser Glu
1               5

<210> SEQ ID NO 142
<211> LENGTH: 9
<212> TYPE: PRT
<213> ORGANISM: Mus musculus

<400> SEQUENCE: 142

Arg Arg Thr Pro Ser Leu Leu Glu Gln
1               5

<210> SEQ ID NO 143
<211> LENGTH: 9
<212> TYPE: PRT
<213> ORGANISM: Homo sapiens

<400> SEQUENCE: 143

His Arg Thr Pro Ser Leu Leu Glu Gln
1               5

<210> SEQ ID NO 144
<211> LENGTH: 10
<212> TYPE: PRT
<213> ORGANISM: Rattus norvegicus
```

```
<400> SEQUENCE: 144

Glu Pro Arg Gly Ser Arg Leu Leu Val Arg
1               5                   10

<210> SEQ ID NO 145
<211> LENGTH: 19
<212> TYPE: PRT
<213> ORGANISM: Homo sapiens

<400> SEQUENCE: 145

Met Asp Asp Gln Arg Asp Leu Ile Ser Asn Asn Glu Gln Leu Pro Met
1               5                   10                  15

Leu Gly Arg

<210> SEQ ID NO 146
<211> LENGTH: 19
<212> TYPE: PRT
<213> ORGANISM: Mus musculus

<400> SEQUENCE: 146

Met Asp Asp Gln Arg Asp Leu Ile Ser Asn His Glu Gln Leu Pro Ile
1               5                   10                  15

Leu Gly Asn

<210> SEQ ID NO 147
<211> LENGTH: 20
<212> TYPE: PRT
<213> ORGANISM: Gallus gallus

<400> SEQUENCE: 147

Met Ala Glu Glu Gln Arg Asp Leu Ile Ser Ser Asp Gly Ser Ser Gly
1               5                   10                  15

Val Leu Pro Ile
            20

<210> SEQ ID NO 148
<211> LENGTH: 23
<212> TYPE: PRT
<213> ORGANISM: Danio rerio

<400> SEQUENCE: 148

Met Glu Pro Asp His Gln Asn Glu Ser Leu Ile Gln Arg Val Pro Ser
1               5                   10                  15

Ala Glu Thr Ile Leu Gly Arg
            20

<210> SEQ ID NO 149
<211> LENGTH: 23
<212> TYPE: PRT
<213> ORGANISM: Danio rerio

<400> SEQUENCE: 149

Met Ser Ser Glu Gly Asn Glu Thr Pro Leu Ile Ser Asp Gln Ser Ser
1               5                   10                  15

Val Asn Met Gly Pro Gln Pro
            20

<210> SEQ ID NO 150
<211> LENGTH: 24
<212> TYPE: PRT
<213> ORGANISM: Trypanosoma brucei
```

<400> SEQUENCE: 150

Arg Pro Arg Arg Arg Thr Glu Glu Asp Glu Leu Leu Pro Glu Ala
1               5                   10                  15

Glu Gly Leu Ile Asp Pro Gln Asn
            20

<210> SEQ ID NO 151
<211> LENGTH: 19
<212> TYPE: PRT
<213> ORGANISM: Homo sapiens

<400> SEQUENCE: 151

Pro Asp Lys His Ser Leu Leu Val Gly Asp Phe Arg Glu Asp Asp
1               5                   10                  15

Thr Ala Leu

<210> SEQ ID NO 152
<211> LENGTH: 9
<212> TYPE: PRT
<213> ORGANISM: Homo sapiens

<400> SEQUENCE: 152

Thr Glu Arg Glu Arg Leu Leu Asn Phe
1               5

<210> SEQ ID NO 153
<211> LENGTH: 8
<212> TYPE: PRT
<213> ORGANISM: Homo sapiens

<400> SEQUENCE: 153

Val Glu Thr Asp Asp Leu Ile Leu
1               5

<210> SEQ ID NO 154
<211> LENGTH: 7
<212> TYPE: PRT
<213> ORGANISM: Caenorhabditis elegans

<400> SEQUENCE: 154

Phe Glu Asn Asp Ser Leu Leu
1               5

<210> SEQ ID NO 155
<211> LENGTH: 9
<212> TYPE: PRT
<213> ORGANISM: Saccharomyces cerevisiae

<400> SEQUENCE: 155

Asn Glu Gln Ser Pro Leu Leu His Asn
1               5

<210> SEQ ID NO 156
<211> LENGTH: 8
<212> TYPE: PRT
<213> ORGANISM: Saccharomyces cerevisiae

<400> SEQUENCE: 156

Ser Glu Gln Thr Arg Leu Val Pro
1               5

<210> SEQ ID NO 157
<211> LENGTH: 8

```
<212> TYPE: PRT
<213> ORGANISM: Saccharomyces cerevisiae

<400> SEQUENCE: 157

Glu Val Asp Leu Asp Leu Leu Lys
1               5

<210> SEQ ID NO 158
<211> LENGTH: 5
<212> TYPE: PRT
<213> ORGANISM: Artificial Sequence
<220> FEATURE:
<223> OTHER INFORMATION: Dileucine-based sorting signal
<220> FEATURE:
<221> NAME/KEY: misc_feature
<222> LOCATION: (2)..(3)
<223> OTHER INFORMATION: Xaa can be any naturally occurring amino acid

<400> SEQUENCE: 158

Asp Xaa Xaa Leu Leu
1               5

<210> SEQ ID NO 159
<211> LENGTH: 13
<212> TYPE: PRT
<213> ORGANISM: Homo sapiens

<400> SEQUENCE: 159

Ser Phe His Asp Asp Ser Asp Glu Asp Leu Leu His Ile
1               5                   10

<210> SEQ ID NO 160
<211> LENGTH: 13
<212> TYPE: PRT
<213> ORGANISM: Bos taurus

<400> SEQUENCE: 160

Thr Phe His Asp Asp Ser Asp Glu Asp Leu Leu His Val
1               5                   10

<210> SEQ ID NO 161
<211> LENGTH: 13
<212> TYPE: PRT
<213> ORGANISM: Oryctolagus cuniculus

<400> SEQUENCE: 161

Ser Phe His Asp Asp Ser Asp Glu Asp Leu Leu Asn Ile
1               5                   10

<210> SEQ ID NO 162
<211> LENGTH: 13
<212> TYPE: PRT
<213> ORGANISM: Gallus gallus

<400> SEQUENCE: 162

Ser Phe His Asp Asp Ser Asp Glu Asp Leu Leu Asn Val
1               5                   10

<210> SEQ ID NO 163
<211> LENGTH: 13
<212> TYPE: PRT
<213> ORGANISM: Homo sapiens

<400> SEQUENCE: 163

Glu Glu Ser Glu Glu Arg Asp Asp His Leu Leu Pro Met
1               5                   10
```

```
<210> SEQ ID NO 164
<211> LENGTH: 13
<212> TYPE: PRT
<213> ORGANISM: Gallus gallus

<400> SEQUENCE: 164

Asp Glu Ser Glu Glu Arg Asp Asp His Leu Leu Pro Met
1               5                   10

<210> SEQ ID NO 165
<211> LENGTH: 12
<212> TYPE: PRT
<213> ORGANISM: Homo sapiens

<400> SEQUENCE: 165

Gly Tyr His Asp Asp Ser Asp Glu Asp Leu Leu Glu
1               5                   10

<210> SEQ ID NO 166
<211> LENGTH: 13
<212> TYPE: PRT
<213> ORGANISM: Homo sapiens

<400> SEQUENCE: 166

Ile Thr Gly Phe Ser Asp Asp Val Pro Met Val Ile Ala
1               5                   10

<210> SEQ ID NO 167
<211> LENGTH: 13
<212> TYPE: PRT
<213> ORGANISM: Hydra vulgaris

<400> SEQUENCE: 167

Ile Asn Arg Phe Ser Asp Asp Glu Pro Leu Val Val Ala
1               5                   10

<210> SEQ ID NO 168
<211> LENGTH: 13
<212> TYPE: PRT
<213> ORGANISM: Homo sapiens

<400> SEQUENCE: 168

Met Leu Glu Ala Ser Asp Asp Glu Ala Leu Leu Val Cys
1               5                   10

<210> SEQ ID NO 169
<211> LENGTH: 13
<212> TYPE: PRT
<213> ORGANISM: Homo sapiens

<400> SEQUENCE: 169

Lys Asn Glu Thr Ser Asp Asp Glu Ala Leu Leu Leu Cys
1               5                   10

<210> SEQ ID NO 170
<211> LENGTH: 12
<212> TYPE: PRT
<213> ORGANISM: Mus musculus

<400> SEQUENCE: 170

Trp Val Val Glu Ala Glu Asp Glu Pro Leu Leu Ala
1               5                   10
```

```
<210> SEQ ID NO 171
<211> LENGTH: 12
<212> TYPE: PRT
<213> ORGANISM: Homo sapiens

<400> SEQUENCE: 171

Trp Val Ala Glu Ala Glu Asp Glu Pro Leu Leu Thr
1               5                   10

<210> SEQ ID NO 172
<211> LENGTH: 12
<212> TYPE: PRT
<213> ORGANISM: Homo sapiens

<400> SEQUENCE: 172

His Asp Asp Phe Ala Asp Asp Ile Ser Leu Leu Lys
1               5                   10

<210> SEQ ID NO 173
<211> LENGTH: 13
<212> TYPE: PRT
<213> ORGANISM: Mus musculus

<400> SEQUENCE: 173

Gly Arg Asp Ser Pro Glu Asp His Ser Leu Leu Val Asn
1               5                   10

<210> SEQ ID NO 174
<211> LENGTH: 12
<212> TYPE: PRT
<213> ORGANISM: Peromyscus maniculatus

<400> SEQUENCE: 174

Val Arg Cys His Pro Glu Asp Asp Arg Leu Leu Gly
1               5                   10

<210> SEQ ID NO 175
<211> LENGTH: 13
<212> TYPE: PRT
<213> ORGANISM: Homo sapiens

<400> SEQUENCE: 175

His Arg Val Ser Gln Asp Asp Leu Asp Leu Leu Thr Ser
1               5                   10

<210> SEQ ID NO 176
<211> LENGTH: 13
<212> TYPE: PRT
<213> ORGANISM: Homo sapiens

<400> SEQUENCE: 176

Ala Ser Val Ser Leu Leu Asp Asp Glu Leu Met Ser Leu
1               5                   10

<210> SEQ ID NO 177
<211> LENGTH: 13
<212> TYPE: PRT
<213> ORGANISM: Homo sapiens

<400> SEQUENCE: 177

Ala Ser Ser Gly Leu Asp Asp Leu Asp Leu Leu Gly Lys
1               5                   10

<210> SEQ ID NO 178
<211> LENGTH: 13
```

```
<212> TYPE: PRT
<213> ORGANISM: Homo sapiens

<400> SEQUENCE: 178

Val Gln Asn Pro Ser Ala Asp Arg Asn Leu Leu Asp Leu
1               5                   10

<210> SEQ ID NO 179
<211> LENGTH: 13
<212> TYPE: PRT
<213> ORGANISM: Homo sapiens

<400> SEQUENCE: 179

Asn Ala Leu Ser Trp Leu Asp Glu Glu Leu Leu Cys Leu
1               5                   10

<210> SEQ ID NO 180
<211> LENGTH: 13
<212> TYPE: PRT
<213> ORGANISM: Drosophila sp.

<400> SEQUENCE: 180

Thr Val Asp Ser Ile Asp Asp Val Pro Leu Leu Ser Asp
1               5                   10

<210> SEQ ID NO 181
<211> LENGTH: 13
<212> TYPE: PRT
<213> ORGANISM: Mus musculus

<400> SEQUENCE: 181

Gln Glu Glu Cys Pro Ser Asp Ser Glu Glu Asp Glu Gly
1               5                   10

<210> SEQ ID NO 182
<211> LENGTH: 13
<212> TYPE: PRT
<213> ORGANISM: Mus musculus

<400> SEQUENCE: 182

Arg Asp Arg Asp Tyr Asp Glu Asp Glu Asp Asp Ile
1               5                   10

<210> SEQ ID NO 183
<211> LENGTH: 15
<212> TYPE: PRT
<213> ORGANISM: Mus musculus

<400> SEQUENCE: 183

Leu Asp Glu Thr Glu Asp Asp Glu Leu Glu Tyr Asp Asp Glu Ser
1               5                   10                  15

<210> SEQ ID NO 184
<211> LENGTH: 10
<212> TYPE: PRT
<213> ORGANISM: Homo sapiens

<400> SEQUENCE: 184

Lys Asp Pro Asp Glu Val Glu Thr Glu Ser
1               5                   10

<210> SEQ ID NO 185
<211> LENGTH: 13
<212> TYPE: PRT
<213> ORGANISM: Homo sapiens
```

-continued

<400> SEQUENCE: 185

His Glu Phe Gln Asp Glu Thr Asp Thr Glu Glu Glu Thr
1               5                   10

<210> SEQ ID NO 186
<211> LENGTH: 14
<212> TYPE: PRT
<213> ORGANISM: Homo sapiens

<400> SEQUENCE: 186

Gln Glu Lys Glu Asp Asp Gly Ser Glu Ser Glu Glu Glu Tyr
1               5                   10

<210> SEQ ID NO 187
<211> LENGTH: 9
<212> TYPE: PRT
<213> ORGANISM: Homo sapiens

<400> SEQUENCE: 187

Gly Glu Asp Glu Glu Ser Glu Ser Asp
1               5

<210> SEQ ID NO 188
<211> LENGTH: 12
<212> TYPE: PRT
<213> ORGANISM: Homo sapiens

<400> SEQUENCE: 188

Gly Glu Asp Ser Asp Glu Glu Pro Asp His Glu Glu
1               5                   10

<210> SEQ ID NO 189
<211> LENGTH: 11
<212> TYPE: PRT
<213> ORGANISM: Homo sapiens

<400> SEQUENCE: 189

Leu Glu Asp Asp Ser Asp Glu Glu Glu Asp Phe
1               5                   10

<210> SEQ ID NO 190
<211> LENGTH: 9
<212> TYPE: PRT
<213> ORGANISM: Human cytomegalovirus

<400> SEQUENCE: 190

Lys Asp Ser Asp Glu Glu Glu Asn Val
1               5

<210> SEQ ID NO 191
<211> LENGTH: 13
<212> TYPE: PRT
<213> ORGANISM: Human herpesvirus 3

<400> SEQUENCE: 191

Phe Glu Asp Ser Glu Ser Thr Asp Thr Glu Glu Glu Phe
1               5                   10

<210> SEQ ID NO 192
<211> LENGTH: 9
<212> TYPE: PRT
<213> ORGANISM: Human immunodeficiency virus type 1

<400> SEQUENCE: 192

```
<210> SEQ ID NO 193
<211> LENGTH: 22
<212> TYPE: PRT
<213> ORGANISM: Saccharomyces cerevisiae

<400> SEQUENCE: 193

Ala Asp Asp Leu Glu Ser Gly Leu Gly Ala Glu Asp Asp Leu Glu Gln
1               5                   10                  15

Asp Glu Gln Leu Glu Gly
            20

<210> SEQ ID NO 194
<211> LENGTH: 12
<212> TYPE: PRT
<213> ORGANISM: Saccharomyces cerevisiae

<400> SEQUENCE: 194

Thr Glu Ile Asp Glu Ser Phe Glu Met Thr Asp Phe
1               5                   10

<210> SEQ ID NO 195
<211> LENGTH: 18
<212> TYPE: PRT
<213> ORGANISM: Saccharomyces cerevisiae

<400> SEQUENCE: 195

Thr Glu Pro Glu Glu Val Glu Asp Phe Asp Phe Asp Leu Ser Asp Glu
1               5                   10                  15

Asp His

<210> SEQ ID NO 196
<211> LENGTH: 15
<212> TYPE: PRT
<213> ORGANISM: Saccharomyces cerevisiae

<400> SEQUENCE: 196

Phe Glu Ile Glu Glu Asp Asp Val Pro Thr Leu Glu Glu Glu His
1               5                   10                  15

<210> SEQ ID NO 197
<211> LENGTH: 4
<212> TYPE: PRT
<213> ORGANISM: Artificial Sequence
<220> FEATURE:
<223> OTHER INFORMATION: Intracellular retention signal

<400> SEQUENCE: 197

His Asp Glu Leu
1
```

Leu Glu Ala Gln Glu Glu Glu Val
1               5

NUCLEIC ACID CONSTRUCT

CROSS-REFERENCE TO RELATED APPLICATIONS

This application is a U.S. national phase of International Application No. PCT/GB2016/051164, filed on Apr. 26, 2016, which claims priority benefit to Application No. 1507104.6, filed in the United Kingdom on Apr. 27, 2015.

FIELD OF THE INVENTION

The present invention relates to constructs and approaches for modulating the relative expression of polypeptides co-expressed from a single vector. In particular, the invention relates to modulating the expression of a transmembrane protein co-expressed from a single vector with a second polypeptide.

INCORPORATION BY REFERENCE OF MATERIAL SUBMITTED ELECTRONICALLY

This application includes a Sequence Listing as a part of the disclosure, submitted as a text file named "52471_Seq-listing.txt", created on Sep. 25, 2017, 52,273 bytes in size. The subject matter of the Sequence Listing is incorporated herein in its entirety by reference.

BACKGROUND TO THE INVENTION

It is often desirable to express different proteins from the same vector since multiple transduction of the same cell is difficult, expensive and unpredictable. Different methods have therefore been developed to allow co-expression of two proteins from a single vector (see FIG. 1).

Initial attempts used two different promoters within the same cassette. This results in two separate transcripts each of which code for a separate protein. This is a difficult approach for a number of reasons. A key problem is "promoter interference" whereby one promoter dominates and causes silencing of the second promoter. In addition, different promoters work differently in different cellular contexts and this makes consistent "tuning" of the relative expression of each transgene difficult to achieve.

An alternative approach is to use an Internal Ribosome Entry sequence (IRES). Here, a single transcript is generated. The IRES sequence in the transcript is placed between the open reading frames for the two transgenes and mimics an mRNA cap structure. Hence, the ribosome either initiates translation at the 5' cap or the IRES resulting in expression of two separate proteins. A key limitation with this approach is the inability to control relative expression. The 3' transcript is typically expressed less than the 5' one, but the ratio of expression is difficult to predict and tune.

A further approach has been provided following characterization of the role of foot-and-mouth-disease virus (FMDV) 2A peptide in allowing FMDV (and related viruses) to express multiple proteins from a single open reading frame (ORF) (Donnelly et al; *J. Gen. Virol.*; 82, 1027-1041 (2001)). The 2A peptide (and homologs) cleaves at very high efficiency immediately after translation of the ORF, enabling the expression of multiple peptides from a single ORF. A problem with the use of the 2A peptide to cleave between different peptides in the same ORF is that expression is limited to a 1:1 ratio.

Thus there is a need for alternative methods for expressing more than one protein from a single vector which are not associated with the disadvantages described above.

SUMMARY OF ASPECTS OF THE INVENTION

The present invention is based on the determination that, when a transmembrane protein is co-expressed with a second protein as a polyprotein which after translation is subsequently cleaved to separate both proteins, the incorporation of an intracellular retention signal in the transmembrane protein allows the cell surface expression of the transmembrane protein to be modulated relative to the second protein by reducing its trafficking to the cell surface and/or by reducing its half-life at the cell surface. This need not be limited to a pair of transgenes, but may be used to allow control of the relative expression of multiple proteins initially translated as a polyprotein.

As used herein, 'polyprotein' refers to a polypeptide sequence translated from a single nucleic acid construct as a single entity, but which comprises polypeptide sequences which are subsequently separated and which function as discrete entities (e.g. separate proteins).

Thus in a first aspect the present invention provides a nucleic acid construct comprising the following structure:

A-X-B in which
A and B are nucleic acid sequences encoding a first and a second protein of interest (POI); and
X is a nucleic acid sequence which encodes a cleavage site,
wherein either the first or second POI is a transmembrane protein which comprises an intracellular retention signal.

The intracellular retention signal is heterologous to the transmembrane protein i.e. it does not occur in the "wild-type" version of the transmembrane protein (or part thereof) and is introduced by recombinant means. The intracellular retention signal may be synthetic or derivable from another organism or another protein.

The endodomain of the transmembrane protein may comprise the intracellular retention signal.

The intracellular retention signal may direct the transmembrane protein away from the secretory pathway and/or to a membrane-bound intracellular compartment such as a lysozomal, endosomal or Golgi compartment.

The intracellular retention signal may, for example, be a tyrosine-based sorting signal, a dileucine-based sorting signal, an acidic cluster signal, a lysosomal avoidance signal, an NPFX'(1,2)D-Type signal (SEQ ID NO: 50), a KDEL (SEQ ID NO: 51), a KKX'X' (SEQ ID NO: 52) or a KX'KX'X' (SEQ ID NO: 53) signal (wherein X' is any amino acid).

The intracellular retention signal may comprise a sequence selected from the group of: NPX'Y (SEQ ID NO: 54), YX'X'Z' (SEQ ID NO: 55), [DE]X'X'X'L[LI] (SEQ ID NO: 56), DX'X'LL (SEQ ID NO: 57), DP[FW] (SEQ ID NO: 58), FX'DX'F (SEQ ID NO: 59), NPF, LZX'Z[DE] (SEQ ID NO: 60), LLDLL (SEQ ID NO: 61), PWDLW (SEQ ID NO: 62), KDEL (SEQ ID NO: 51), KKX'X' (SEQ ID NO: 52) or KX'KX'X' (SEQ ID NO: 53);
wherein X' is any amino acid and Z' is an amino acid with a bulky hydrophobic side chain.

The intracellular retention signal may comprise any of the sequences shown in Tables 1 to 5.

The intracellular retention signal may comprise the Tyrosinase-related protein (TYRP)-1 intracellular retention signal. The intracellular retention signal may comprise the TYRP-1 intracellular domain. The intracellular retention signal may comprise the sequence NQPLLTD (SEQ ID NO: 35).

The intracellular retention signal may comprise the Adenoviral E3/19K intracellular retention signal. The intracellular retention signal may comprise the E3/19K cytosolic domain. The intracellular retention signal may comprise the sequence KYKSRRSFIDEKKMP (SEQ ID NO: 36); or DEKKMP (SEQ ID NO: 37).

The intracellular retention signal may be proximal or distal to a transmembrane domain of the transmembrane protein.

X may be a nucleic acid sequence encoding a self-cleaving peptide, a furin cleavage site or a Tobacco Etch Virus cleavage site.

X may be a nucleic acid sequence encoding a 2A self-cleaving peptide from an aphtho- or a cardiovirus or a 2A-like peptide.

The transmembrane protein may be any transgenically expressed transmembrane protein.

The transmembrane protein may be selected from a list of: excitatory receptors such as 41 BB, OX40, CD27, CD28 and related molecules; or inhibitory receptors such as PD1, CTLA4, LAIR1, CD22 and related molecules; or cytokine receptor molecules such as IL1R, IL2R, IL7R, IL15R and related molecules; or homing molecules such as N-CAM, V-CAM, L1-CAM, LFA-1, CDH1-3, Selectins or Integrins;

The transmembrane protein may be a synthetic protein such as a suicide gene or a marker gene.

The transmembrane protein may be or comprise the α and/or β chains of a T-cell receptor.

The transmembrane protein may be a chimeric-antigen receptor (CAR).

Either or both of the first and second POIs may be a transmembrane protein; and either or both of the transmembrane proteins may comprise an intracellular retention signal as defined herein.

Either or both of the first and second POIs may be a single pass transmembrane protein, such a type I transmembrane protein.

The amount of a transmembrane protein which comprises an intracellular retention signal which is expressed at the cell surface may be, for example, less than 90%, 70%, 50% or 30% compared to a transmembrane protein expressed from the same nucleic acid construct which does not comprise an intracellular retention signal.

The invention also provides nucleic acid construct encoding more than two proteins of interest. For example, in one embodiment, the invention provides a nucleic acid construct comprising the following structure:

A-X-B-Y-C in which
A, B and C are nucleic acid sequences encoding first, second and third polypeptides of interest (POIs); and
X and Y are nucleic acid sequences which may be the same or different, each of which encodes a cleavage site,
wherein at least two of the POIs are transmembrane proteins which comprise an intracellular retention signal.

In this embodiment, the at least two POIs may:
(a) comprise different intracellular retention signals; and/or
(b) have the intracellular retention signal located at a different position in the POI, such that when the nucleic acid is expressed in a cell, there is differential relative expression of the at least two POIs at the cell surface.

In a second aspect the present invention provides a vector comprising a nucleic acid construct according to the first aspect of the invention.

The vector may be a retroviral vector or a lentiviral vector or a transposon.

In a third aspect the present invention provides a cell comprising a nucleic acid construct according to the first aspect of the invention or a vector according to the second aspect of the invention.

The invention further relates to a method for modulating the relative cell surface expression of a transmembrane protein expressed as a polyprotein from a single nucleic acid with a second protein by including an intracellular retention signal in the nucleic acid sequence which encodes the transmembrane protein.

The inclusion of an intracellular retention signal in a transmembrane protein reduces the amount of the transmembrane protein expressed on the cell surface. As such, the relative expression level of a transmembrane protein derived from a polyprotein including a second polypeptide can be modulated. Where the transmembrane protein is only active at the cell surface (or predominantly active at the cell surface), reducing the relative cell surface expression of the protein also reduces its relative activity.

This invention can be extended to modulate the relative expression of three or more proteins expressed as a concatenated polypeptide, separated by cleavage sites and relative surface expression dictated by retention signals of differing activity.

A construct was generated which co-expresses an anti-CD19 and an anti-CD33 CAR using a FMD-2A like peptide. Two variants of this construct were also generated: in the first variant, the di-leucine motif from TYRP1 was inserted into the anti-CD19 CAR endodomain just proximal to the TM domain; in the second variant the same TYRP1 di-lecuine motif was attached to the carboxy-terminus of the anti-CD19 CAR endodomain. PBMCs were isolated from blood and stimulated using PHA and IL-2. Two days later the cells were transduced on retronectin coated plates with retro virus containing the different CD19:CD33 CAR constructs. On day 5 the expression level of the two CARs translated by the construct was evaluated via flow cytometry using recombinant CD19-Fc and CD33-Fc fusions. A. Shows cartoon of the synthetic gene constructed to allow co-expression; B. Shows a cartoon of the subsequent pairs of proteins generated by the three constructs; C. Shows expression of the two receptors by flow-cytometry. In the original construct, both CARs are equally expressed. With incorporation of the di-leucine motif distally in the endodomain of the anti-CD19 CAR, the CD33 CAR expression remains constant but the CD19 expression drops to intermediate levels. With incorporation of the di-leucine motif proximally in the endodomain of the anti-CD19 CAR, the CD33 CAR expression remains constant, but the CD19 expression drops to low levels.

Figure 4:
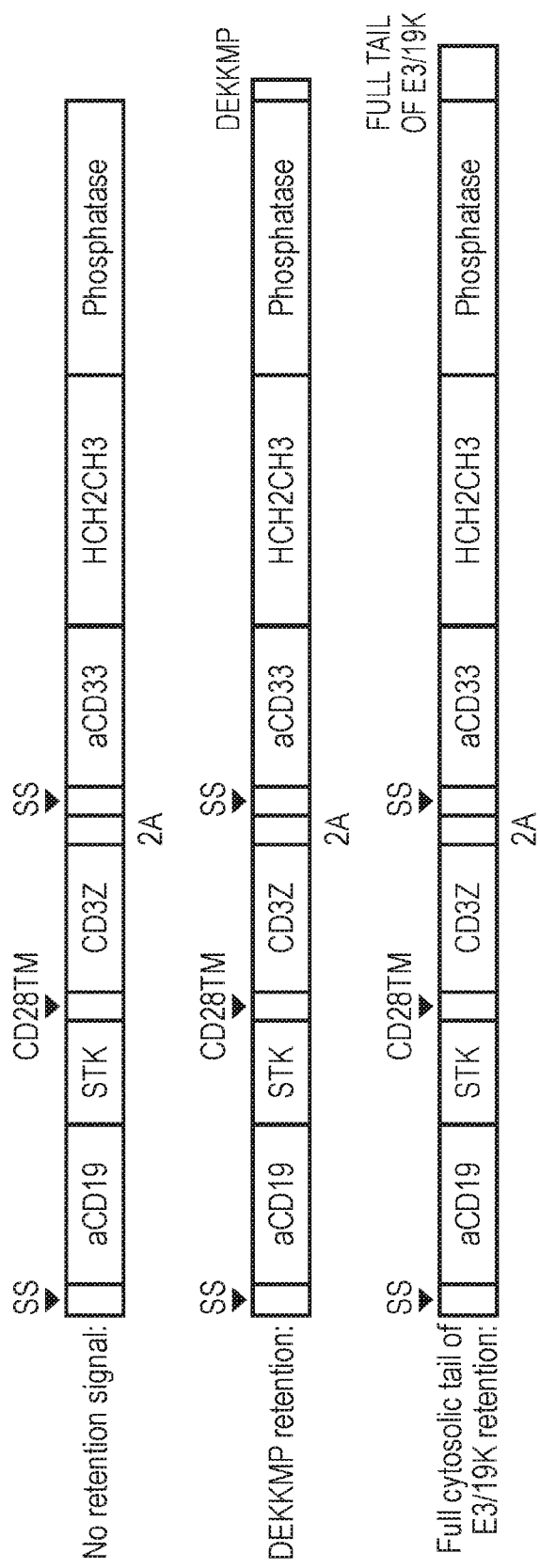

FIG. 4: Retention signal from cytosolic tail of E3/19K

A construct was generated which co-expresses an anti-CD19 and an anti-CD33 CAR using a FMD-2A like peptide. Two variants of this construct were also generated: in the first variant, the last 6aa from E3/19K (DEKKMP (SEQ ID NO: 37)), which were found to be critical for its Golgi/ER retention ability, were attached to the carboxy-terminus of the anti-CD33 CAR endodomain; in the second variant, the entire cytosolic tail of adenovirus E3/19K protein was attached to the carboxy-terminus of the anti-CD33 CAR endodomain FIG. 5: Functionality of E3/19K retention signal The constructs shown in FIG. 4 were transfected into 293T cells and the expression level of the two CARs translated by the construct was evaluated via flow cytometry using recombinant CD19-Fc and CD33-Fc fusions. A clear retention was observed when the full length adenovirus E3/19K protein, or the DEKKMP (SEQ ID NO: 37) motif was placed on the anti-CD33 receptor. The anti-CD19 receptor expression levels were unaffected.

DETAILED DESCRIPTION

The present invention provides a nucleic acid construct comprising the following structure:

A-X-B in which;
A and B are nucleic acid sequences encoding a first and a second polypeptide of interest (POI); and
X is a nucleic acid sequence which encodes a cleavage site, wherein either the first or second POI is a transmembrane protein which comprises an intracellular retention signal.

Transmembrane Protein

The present invention enables modulation of the relative expression of a transmembrane surface protein. The transmembrane surface protein is a protein which, in the absence of an intracellular retention signal, is expressed at the cell surface. When expressed at the cell surface at least one domain of the transmembrane protein is exoplasmic (i.e. on the exterior of the cell).

The transmembrane protein may be a single-pass transmembrane protein, i.e. it may comprise a single transmembrane domain or it may comprise multiple transmembrane domains.

Transmembrane proteins may be classified by topology i.e. with reference to the position of the N- and C-terminal domains. Types I, II, and III transmembrane proteins are single-pass molecules, while type IV trans-membrane proteins are multiple-pass molecules. Type I transmembrane proteins are anchored to the lipid membrane with a stop-transfer anchor sequence and have their N-terminal domains targeted to the ER lumen during synthesis (and the extracellular space, when the mature form is located on the plasma membrane). Type II and III are anchored with a signal-anchor sequence, with type II being targeted to the ER lumen with its C-terminal domain, while type III have their N-terminal domains targeted to the ER lumen. Type IV is subdivided into IV-A, with their N-terminal domains targeted to the cytosol and IV-B, with an N-terminal domain targeted to the lumen.

The transmembrane protein(s) of the present invention may be any of the types I-IV.

The transmembrane domain may be any protein structure which is thermodynamically stable in a membrane. This is typically an alpha helix comprising of several hydrophobic residues. The transmembrane domain of any transmembrane protein can be used to supply the transmembrane portion. The presence and span of a transmembrane domain of a protein can be determined by those skilled in the art using the TMHMM algorithm (http://www.cbs.dtu.dk/services/TMHMM-2.0/). Further, given that the transmembrane domain of a protein is a relatively simple structure, i.e., a polypeptide sequence predicted to form a hydrophobic alpha helix of sufficient length to span the membrane, an artificially designed TM domain may also be used (U.S. Pat. No. 7,052,906 B1 describes synthetic transmembrane components).

The transmembrane domain may be derived from CD28, which gives good stability.

The structure and processing of Type I transmembrane proteins is well known in the art. Such proteins typically comprise an extracellular domain, a transmembrane domain and an intracellular endodomain and are single-pass molecules with a single α-helix passing through the cell membrane.

Type I transmembrane proteins typically have a signal peptide which is quickly recognized by the endoplasmic reticulum (ER) and the protein in translation is therefore quickly re-directed into the ER. A hydrophobic helix locks then anchors the protein in the membrane of the ER.

As mentioned above, Type I transmembrane proteins are anchored to the lipid membrane with a stop-transfer anchor sequence. The stop-transfer sequence halts the further translocation of the polypeptide and acts as a transmembrane anchor.

As used herein, the term Type I transmembrane protein encompasses any protein which comprises a Type I transmembrane domain and a stop-transfer anchor sequence and is, in the absence of an exogenous intracellular retention signal, targeted for expression on the cell surface.

Various type 1 transmembrane proteins which are suitable for use in the present invention are known in the art. Such proteins include, but are not limited to inhibitory receptors, stimulatory receptors, cytokine receptors and G-Proteins.

The transmembrane protein(s) may be a T-cell receptor α or β chain.

The transmembrane protein(s) may be a Chimeric Antigen Receptor (CAR).

CARs are proteins which graft an antigen binding domain to the effector function of a T-cell. Their usual form is that of a type I transmembrane domain protein with an antigen recognizing amino terminus, a spacer, a transmembrane domain all connected to a compound endodomain which transmits T-cell survival and activation signals.

The antigen binding domain may be derived from an antibody or antibody mimetic, or it may be another entity which specifically binds the antigen, such as a ligand.

The most common form of these molecules are fusions of single-chain variable fragments (scFv) derived from monoclonal antibodies which recognize a target antigen, fused via a spacer and a trans-membrane domain to a signaling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers.

It is also possible for the signalling endodomain to be present on a separate molecule. Th term "CAR" in connection with the present invention also encompasses a molecule which comprises an antigen binding domain connected to a transmembrane domain. Such a CAR may be capable of interacting with an intracellular signalling domain in order to stimulate T-cell activation.

In the present invention, either of the nucleic acid sequences A or B may be a nucleic acid sequence which encodes a transmembrane protein comprising an intracellular retention signal.

Most transmembrane proteins of interest are only active, or are predominantly active when at the cell membrane. Therefore causing a proportion of the protein to be retained intracellularly reduces the relative expression of the protein at the cell surface and therefore reduces the relative activity of the protein.

Signal Sequence

The transmembrane protein may also comprise a signal sequence so that when the transmembrane protein is expressed inside a cell the nascent protein is directed to the endoplasmic reticulum (ER).

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

Cleavage Site

The present nucleic acid construct comprises a sequence encoding a cleavage site positioned between nucleic acid sequences which encode first and second polypeptides, such that first and second polypeptides can be expressed as separate entities.

The cleavage site may be any sequence which enables the polypeptide comprising the first and second POIs to become separated.

The term "cleavage" is used herein for convenience, but the cleavage site may cause the first and second POIs to separate into individual entities by a mechanism other than classical cleavage. For example, for the Foot-and-Mouth disease virus (FMDV) 2A self-cleaving peptide (see below), various models have been proposed for to account for the "cleavage" activity: proteolysis by a host-cell proteinase, autoproteolysis or a translational effect (Donnelly et al (2001) J. Gen. Virol. 82:1027-1041). The exact mechanism of such "cleavage" is not important for the purposes of the present invention, as long as the cleavage site, when positioned between nucleic acid sequences which encode first and second polypeptides, causes the first and second polypeptides to be expressed as separate entities.

The cleavage site may be a furin cleavage site.

Furin is an enzyme which belongs to the subtilisin-like proprotein convertase family. The members of this family are proprotein convertases that process latent precursor proteins into their biologically active products. Furin is a calcium-dependent serine endoprotease that can efficiently cleave precursor proteins at their paired basic amino acid processing sites. Examples of furin substrates include proparathyroid hormone, transforming growth factor beta 1 precursor, proalbumin, pro-beta-secretase, membrane type-1 matrix metalloproteinase, beta subunit of pro-nerve growth factor and von Willebrand factor. Furin cleaves proteins just downstream of a basic amino acid target sequence (canonically, Arg-X-(Arg/Lys)-Arg') and is enriched in the Golgi apparatus.

The cleavage site may be a Tobacco Etch Virus (TEV) cleavage site.

TEV protease is a highly sequence-specific cysteine protease which is chymotrypsin-like proteases. It is very specific for its target cleavage site and is therefore frequently used for the controlled cleavage of fusion proteins both in vitro and in vivo. The consensus TEV cleavage site is ENLYFQ\S (where '\' denotes the cleaved peptide bond). Mammalian cells, such as human cells, do not express TEV protease. Thus in embodiments in which the present nucleic acid construct comprises a TEV cleavage site and is expressed in a mammalian cell—exogenous TEV protease must also expressed in the mammalian cell.

The cleavage site may encode a self-cleaving peptide.

A 'self-cleaving peptide' refers to a peptide which functions such that when the polypeptide comprising the first and second POIs and the self-cleaving peptide is produced, it is immediately "cleaved" or separated into distinct and discrete first and second polypeptides without the need for any external cleavage activity.

The self-cleaving peptide may be a 2A self-cleaving peptide from an aphtho- or a cardiovirus. The primary 2A/2B cleavage of the aptho- and cardioviruses is mediated by 2A "cleaving" at its own C-terminus. In apthoviruses, such as foot-and-mouth disease viruses (FMDV) and equine rhinitis A virus, the 2A region is a short section of about 18 amino acids, which, together with the N-terminal residue of protein 2B (a conserved proline residue) represents an autonomous element capable of mediating "cleavage" at its own C-terminus.

The C-terminal 19 amino acids of the longer cardiovirus protein, together with the N-terminal proline of 2B mediate "cleavage" with an efficiency approximately equal to the apthovirus FMDV 2a sequence. Cardioviruses include encephalomyocarditis virus (EMCV) and Theiler's murine encephalitis virus (TMEV).

Mutational analysis of EMCV and FMDV 2A has revealed that the motif DxExNPGP (SEQ ID NO: 65) is intimately involved in "cleavage" activity (Donelly et al (2001) as above).

The cleavage site of the present invention may comprise the amino acid sequence: $Dx_1Ex_2NPGP$ (SEQ ID NO: 66), where $x_1$ and $x_2$ are any amino acid. $X_1$ may be selected from the following group: I, V, M and S. $X_2$ may be selected from the following group: T, M, S, L, E, Q and F.

For example, the cleavage site may comprise one of the amino acid sequences shown in Table 1.

TABLE 1

| Motif | Present in: |
|---|---|
| DIETNPGP (SEQ ID No. 1) | Picornaviruses EMCB, EMCD, EMCPV21 |
| DVETNPGP (SEQ ID No. 2) | Picornaviruses MENGO and TM EBEAN; Insect virus DCV, ABPV |
| DVEMNPGP (SEQ ID No. 3) | Picornaviruses TMEGD7 and TMEBEAN |
| DVESNPGP (SEQ ID No. 4) | Picornaviruses FMDA10, FMDA12, FMDC1, FMD01K, FM DSAT3, FMDVSAT2, ERAV; Insect virus CrPV |
| DMESNPGP (SEQ ID No. 5) | Picornavirus FMDV01G |
| DVELNPGP (SEQ ID No. 6) | Picornavirus ERBV; Porcine rotavirus |
| DVEENPGP (SEQ ID No. 7) | Picornavirus PTV-1; Insect virus TaV; Trypanosoma TSR1 |
| DIELNPGP (SEQ ID No. 8) | Bovine Rotavirus, human rotavirus |
| DIEQNPGP (SEQ ID No. 9) | Trypanosoma AP endonuclease |
| DSEFNPGP (SEQ ID No. 10) | Bacterial sequence *T. maritima* |

The cleavage site, based on a 2A sequence may be, for example 15-22 amino acids in length. The sequence may comprise the C-terminus of a 2A protein, followed by a proline residue (which corresponds to the N-terminal proline of 2B).

Mutational studies have also shown that, in addition to the naturally occurring 2A sequences, some variants are also active. The cleavage site may correspond to a variant sequence from a naturally occurring 2A polypeptide, have one, two or three amino acid substitutions, which retains the capacity to induce the "cleavage" of a polyprotein sequence into two or more separate proteins.

The cleavage sequence may be selected from the following which have all been shown to be active to a certain extent (Donnelly et al (2001) as above):

(SEQ ID No. 11)
LLNFDLLKLAGDVESNPGP (SEQ ID No. 12)
LLNFDLLKLAGDVQSNPGP

-continued (SEQ ID No. 13)
LLNFDLLKLAGDVEINPGP (SEQ ID No. 14)
LLNFDLLKLAGDVEFNPGP (SEQ ID No. 15)
LLNFDLLKLAGDVESHPGP (SEQ ID No. 16)
LLNFDLLKLAGDVESEPGP (SEQ ID No. 17)
LLNFDLLKLAGDVESQPGP (SEQ ID No. 18)
LLNFDLLKLAGDVESNPGG Based on the sequence of the DxExNPGP (SEQ ID NO: 65) "a motif, "2A-like" sequences have been found in picornaviruses other than aptho- or cardioviruses, 'picornavirus-like' insect viruses, type C rotaviruses and repeated sequences within *Trypanosoma* spp and a bacterial sequence (Donnelly et al (2001) as above). The cleavage site may comprise one of these 2A-like sequences, such as:

(SEQ ID No. 19)
YHADYYKQRLIHDVEMNPGP (SEQ ID No. 20)
HYAGYFADLLIHDIETNPGP (SEQ ID No. 21)
QCTNYALLKLAGDVESNPGP (SEQ ID No. 22)
ATNFSLLKQAGDVEENPGP (SEQ ID No. 23)
AARQMLLLLSGDVETNPGP (SEQ ID No. 24)
RAEGRGSLLTCGDVEENPGP (SEQ ID No. 25)
TRAEIEDELIRAGIESNPGP (SEQ ID No. 26)
TRAEIEDELIRADIESNPGP (SEQ ID No. 27)
AKFQIDKILISGDVELNPGP (SEQ ID No. 28)
SSIIRTKMLVSGDVEENPGP (SEQ ID No. 29)
CDAQRQKLLLSGDIEQNPGP (SEQ ID No. 30)
YPIDFGGFLVKADSEFNPGP

The cleavage site may comprise the 2A-like sequence shown as SEQ ID NO: 24 (RAEGRGSLLTCGDVEENPGP).

It has been shown that including an N-terminal "extension" of between 5 and 39 amino acids can increase activity (Donnelly et al (2001) as above). In particular, the cleavage sequence may comprise one of the following sequences or a variant thereof having, for example, up to 5 amino acid changes which retains cleavage site activity:

```
VTELLYRMKRAETYCPRPLAIHPTEARHKQKIVAPVKQTLNFDLLKLAGD     (SEQ ID No. 31)
VESNPGP

LLAIHPTEARHKQKIVAPVKQTLNFDLLKLAGDVESNPGP              (SEQ ID No. 32)

EARHKQKIVAPVKQTLNFDLLKLAGDVESNPGP                     (SEQ ID No. 33)

APVKQTLNFDLLKLAGDVESNPGP                              (SEQ ID No. 34)
INTRACELLULAR RETENTION SIGNAL
```

The nucleic acid construct of the present invention comprises a sequence which encodes a transmembrane protein comprising an intracellular retention signal.

Protein targeting or protein sorting is the biological mechanism by which proteins are transported to the appropriate destinations in the cell or outside of it. Proteins can be targeted to the inner space of an organelle, different intracellular membranes, plasma membrane, or to exterior of the cell via secretion. This delivery process is carried out based on sequence information contain in the protein itself.

Proteins synthesised in the rough endoplasmic reticulum (ER) of eukaryotic cells use the exocytic pathway for transport to their final destinations. Proteins lacking special sorting signals are vectorially transported from the ER via the Golgi and the trans-Golgi network (TGN) to the plasma membrane. Other proteins have targeting signals for incorporation into specific organelles of the exocytic pathway, such as endosomes and lysosomes.

Lysosomes are acidic organelles in which endogenous and internalised macromolecules are degraded by luminal hydolases. Endogenous macromolecules reach the lysosome by being sorted in the TGN from which they are transported to endosomes and then lysosomes.

The targeting signals used by a cell to sort proteins to the correct intracellular location may be exploited by the present invention. The signals may be broadly classed into the following types:
i) endocytosis signals
ii) Golgi retention signals
iii) TGN recycling signals
iv) ER retention signals
v) lysosomal sorting signals 'Intracellular retention signal' refers to an amino acid sequence which directs the protein in which it is encompassed to a cellular compartment other than the cell surface membrane or to the exterior of the cell.

The intracellular retention signal causes a reduction in the amount of the transmembrane protein expressed on the surface of a cell compared to an equivalent, control transmembrane protein which does not comprise an intracellular retention signal.

In other words, the proportion of translated transmembrane protein comprising an intracellular retention signal which is expressed on at the cell surface is less than the proportion of an equivalent amount of an equivalent, translated control transmembrane protein which does not comprise an intracellular retention signal.

For example, the amount of the transmembrane protein comprising an intracellular retention signal which is expressed on the surface of a cell may be less than 75%, less than 50%, less than 25% or less than 10% of the amount of an equivalent control transmembrane protein which does not comprise an intracellular retention signal.

Constructs which express a polyprotein that is subsequently cleaved by a protease are generally limited by the fact the expression of the peptides from the polyprotein is limited to a 1:1 ratio. However, in the present invention, the inclusion of an intracellular retention signal in the transmembrane protein means that its expression on the cell surface can be modulated (e.g. reduced compared to an equivalent control transmembrane protein which does not comprise an intracellular retention signal). As such the ratio of the transmembrane protein which comprises the intracellular retention signal expressed on the cell surface compared to the expression of the second protein expressed in the polyprotein may be, for example about 1:1.5, of from 1:1.5-1:2, 1:2-1:3, 1:3-1:4, 1:4-1:5, or more than 1:5.

The amount of a transmembrane protein expressed on the surface of a cell may be determined using methods which are known in the art, for example flow cytometry or fluorescence microscopy.

The intracellular retention signal may direct the transmembrane protein away from the secretory pathway during translocation from the ER.

The intracellular retention signal may direct the transmembrane protein to an intracellular compartment or complex. The intracellular retention signal may direct the transmembrane protein to a membrane-bound intracellular compartment.

For example, the intracellular retention signal may direct the protein to a lysosomal, endosomal or Golgi compartment (trans-Golgi Network, 'TGN').

Within a normal cell, proteins arising from biogenesis or the endocytic pathway are sorted into the appropriate intracellular compartment following a sequential set of sorting decisions. At the plasma membrane, proteins can either remain at the cell surface or be internalised into endosomes. At the TGN, the choice is between going to the plasma membrane or being diverted to endosomes. In endosomes, proteins can either recycle to the plasma membrane or go to lysosomes. These decisions are governed by sorting signals on the proteins themselves.

Lysosomes are cellular organelles that contain acid hydrolase enzymes that break down waste materials and cellular debris. The membrane around a lysosome allows the digestive enzymes to work at the pH they require. Lysosomes fuse with autophagic vacuoles (phagosomes) and dispense their enzymes into the autophagic vacuoles, digesting their contents.

An endosome is a membrane-bounded compartment inside eukaryotic cells. It is a compartment of the endocytic membrane transport pathway from the plasma membrane to the lysosome and provides an environment for material to be sorted before it reaches the degradative lysosome. Endosomes may be classified as early endosomes, late endosomes, or recycling endosomes depending on the time it takes for endocytosed material to reach them. The intracellular retention signal used in the present invention may direct the protein to a late endosomal compartment.

The Golgi apparatus is part of the cellular endomembrane system, the Golgi apparatus packages proteins inside the cell before they are sent to their destination; it is particularly important in the processing of proteins for secretion.

There is a considerable body of knowledge which has arisen from studies investigating the sorting signals present in known proteins, and the effect of altering their sequence and/or position within the molecule (Bonifacino and Traub (2003) Ann. Rev. Biochem. 72:395-447; Braulke and Bonifacino (2009) Biochimica and Biophysica Acta 1793:605-614; Griffith (2001) Current Biology 11:R226-R228; Mellman and Nelson (2008) Nat Rev Mol Cell Biol. 9:833-845; Dell'Angelica and Payne (2001) Cell 106:395-398; Schafer et al (1995) EMBO J. 14:2424-2435; Trejo (2005) Mol. Pharmacol. 67:1388-1390). Numerous studies have shown that it is possible to insert one or more sorting signals into a protein of interest in order to alter the intracellular location of a protein of interest (Pelham (2000) Meth. Enzymol. 327:279-283).

It is therefore perfectly possible to select a sorting signal having a desired localisation property and include it within a protein of interest in order to direct the intracellular location of that protein. In connection with the present application, it is therefore possible to select a sorting signal having the desired amount of reduction of expression at the plasma membrane.

The optimal position of the sorting signal in the nascent protein of interest may depend on the type of transmembrane protein (i.e. types I-IV) and whether the C-terminus is on the luminal or the cytoplasmic side of the membrane (Goder and Spiess (2001) FEBS Lett 504:87-93). This may readily be determined by considering the position of the sorting signal in its natural protein.

Examples of endocytosis signals include those from the transferrin receptor and the asialoglycoprotein receptor.

Examples of signals which cause TGN-endosome recycling include those form proteins such as the CI- and CD-MPRs, sortilin, the LDL-receptor related proteins LRP3 and LRP10 and β-secretase, GGA1-3, LIMP-II, NCP1, mucolipn-1, sialin, GLUTS and invariant chain.

Examples of TGN retention signals include those from the following proteins which are localized to the TGN: the prohormone processing enzymes furin, PC7, CPD and PAM; the glycoprotein E of herpes virus 3 and TGN38.

Examples of ER retention signals include C-terminal signals such as KDEL(SEQ ID NO: 51), KKXX (SEQ ID NO: 52) or KXKXX (SEQ ID NO: 53) and the RXR(R) (SEQ ID NO: 67) motif of potassium channels. Known ER proteins include the adenovirus E19 protein and ERGIC53.

Examples of lysosomal sorting signals include those found in lysosomal membrane proteins, such as LAMP-1 and LAMP-2, CD63, CD68, endolyn, DC-LAMP, cystinosin, sugar phosphate exchanger 2 and acid phosphatase.

The intracellular retention signal may be from the adenovirus E19 protein. The intracellular retention signal may be from the protein E3/19K, which is also known as E3gp 19 kDa; E19 or GP19K. The intracellular retention signal may comprise the full cytosolic tail of E3/19K, which is shown as SEQ ID NO: 36; or the last 6 amino acids of this tail, which is shown as SEQ ID NO: 37. The present inventors have shown that the last 6 amino acids are particularly important for retention (Example 3 and FIG. 5)

SEQ ID No. 36:
KYKSRRSFIDEKKMP

SEQ ID No. 37:
DEKKMP

Tunability

The relative expression of one or more protein(s) may be fine tuned using the method of the invention by various methods, such as
a) altering the position of the intracellular retention signal in the protein molecule; and/or
b) selecting a particular intracellular retention signal.
Option a) is discussed in more detail below.

With regard to option b), a range of intracellular retention signals is available from the large number of naturally occurring proteins which are sorted to distinct cellular locations inside eukaryotic cells. It is also possible to use "synthetic" intracellular retention signals which comprise one of more of the motifs found in naturally occurring proteins (see next section) and have a similar sorting signal function.

A cascade of signal strength is available, depending on the intracellular location to which the sorting signal sends the relevant protein. Broadly speaking, the more "intracellular" the location directed by the sorting signal, the "stronger" the signal is in terms of lowering the relative expression of the protein.

When a sorting signal directs a protein to the lysosomal compartment, the protein is internalised and degraded by the cell, resulting in relatively little escape to the cell surface.

The protein is degraded and lost from the system once it enters the lysosome. Therefore lysosomal sorting signals, such as LAMP1, are the "strongest" in terms of reducing relative expression at the cell surface.

When a sorting signal directs a protein to be retained in the ER, only a very small proportion of the protein gets to the cell surface. Hence ER retention or recycling signals, such as ER-GIC-53 and KKFF signal are the next most strong, in terms of reducing relative expression at the cell surface.

When a sorting signal directs a protein to the endosomal, Golgi or TGN compartments, then the protein is likely to recycle to some extent between the TGN, the endosomal compartment, and the plasma membrane. These signals provide a more limited level of reduction of expression as a significant proportion of the protein will still reach the plasma membrane.

In general the reduction in expression seen with known sorting signals can be summarised as follows:

Lysosomal sorting signals>ER retention/recycling signals>TGN retention/recycling signals>endocytosis signals.

The tunability using different sorting signals and/or different positions of sorting signals within the protein is especially useful when one considers the expression of multiple proteins, each with their own relative expression. For example, consider a nucleic acid construct having the following structure:

A-X-B-Y-C in which

A, B and C are nucleic acid sequences encoding polypeptides; and

X and Y are nucleic acid sequences encodes cleavage sites.

The nucleic acid construct will encode three proteins A, B and C, any or all of which may be transmembrane proteins. For example, B and C may be transmembrane proteins which comprise an intracellular retention signal. If it is desired for A, B and C to be expressed such that the relative levels are A>B>C, then the nucleic acid sequence A may have no intracellular retention signal, the nucleic acid sequence B may have an intracellular retention signal that causes a small proportion of protein B to be retained in the cell (i.e. not to be expressed at the cell surface), and the nucleic acid sequence C may have an intracellular retention signal that causes a large proportion of protein C to be retained in the cell.

As explained below, differential amounts of intracellular retention, leading to different amounts of cell surface expression may be achieved by:

(a) using different intracellular retention signals for the proteins; and/or
(b) having the intracellular retention signal located at a different position in the proteins.

Signal Types

Numerous proteins which include an intracellular retention signal and are directed to an intracellular compartment are known in the art.

The intracellular retention signal may be a retention signal from a protein which resides in the lysosomal, endosomal or Golgi compartment.

Intracellular retention signals are well known in the art (see, for example, Bonifacino & Traub; Annu. Rev. Biochem.; 2003; 72; 395-447).

The intracellular retention signal may be a tyrosine-based sorting signal, a dileucine-based sorting signal, an acidic cluster signal, a lysosomal avoidance signal, an NPFX'(1, 2)D-Type signal (SEQ ID NO: 50), a KDEL (SEQ ID NO: 51), a KKX'X' (SEQ ID NO: 52) or a KX'KX'X '(SEQ ID NO: 53) signal (wherein X' is any amino acid).

Tyrosine-based sorting signals mediate rapid internalization of transmembrane proteins from the plasma membrane and the targeting of proteins to lysosomes (Bonifacino & Traub; as above). Two types of tyrosine-based sorting signals are represented by the NPX'Y (SEQ ID NO: 54) and YX'X'Z' (SEQ ID NO: 55) consensus motifs (wherein Z' is an amino acid with a bulky hydrophobic side chain).

NPX'Y (SEQ ID NO: 54) signals have been shown to mediate rapid internalization of type I transmembrane proteins, they occur in families such as members of the LDL receptor, integrin β, and β-amyloid precursor protein families.

Examples of NPX'Y (SEQ ID NO: 54) signals are provided in Table 2.

TABLE 2

| NPX'Y (SEQ ID NO: 54) signals | | | |
|---|---|---|---|
| Protein | Species | Sequence | |
| LDL receptor | Human | Tm-10-INFDNPVYQKTT-29 | SEQ ID NO: 68 |
| LRP1 (1) | Human | Tm-21-VEIGNPTYKMYE-64 | SEQ ID NO: 69 |
| LRP1 (2) | Human | Tm-55-TNFTNPVYATLY-33 | SEQ ID NO: 70 |
| LRP1 | Drosophila | Tm-43-GNFANPVYESMY-38 | SEQ ID NO: 71 |
| LRP1 (1) | C. elegans | Tm-54-TTFTNPVYELED-91 | SEQ ID NO: 72 |
| LRP1 (2) | C. elegans | Tm-140-LRVDNPLYDPDS-4 | SEQ ID NO: 73 |
| Megalin (1) | Human | Tm-70-IIFENPMYSARD-125 | SEQ ID NO: 74 |
| Megalin (2) | Human | Tm-144-TNFENPIYAQME-53 | SEQ ID NO: 75 |
| Integrin 13-1 (1) | Human | Tm-18-DTGENPIYKSAV-11 | SEQ ID NO: 76 |
| Integtin 13-1 (2) | Human | Tm-30-TTVVNPKYEGK | SEQ ID NO: 77 |
| Integrin 13 (1) | Drosophila | Tm-26-WDTENPIYKQAT-11 | SEQ ID NO: 78 |
| Integrin 13 (2) | Drosophila | Tm-35-STFKNPMYAGK | SEQ ID NO: 79 |
| APLP1 | Human | Tm-33-HGYENPTYRFLE-3 | SEQ ID NO: 80 |
| APP | Human | Tm-32-NGYENPTYKFFE-4 | SEQ ID NO: 81 |
| APP-like | Drosophila | Tm-38-NGYENPTYKYFE-3 | SEQ ID NO: 82 |
| Insulin receptor | Human | Tm-36-YASSNPEYLSAS-379 | SEQ ID NO: 83 |
| EGR receptor (1) | Human | Tm-434-GSVQNPVYHNQP-96 | SEQ ID NO: 84 |
| EGR receptor (2) | Human | Tm-462-TAVGNPEYLNTV-68 | SEQ ID NO: 85 |

TABLE 2 -continued

NPX'Y (SEQ ID NO: 54) signals

| Protein | Species | Sequence | |
|---|---|---|---|
| EGR receptor (3) | Human | Tm-496-ISLDNPDYQQDF-34 | SEQ ID NO: 86 |

Numbers in parentheses indicate motifs that are present in more than one copy within the same protein.
The signals in this and other tables should be considered examples.
Key residues are indicated in bold type.
Numbers of amino acids before (i.e., amino-terminal) and after (i.e., carboxy-terminal) the signals are indicated.
Abbreviations: Tm, transmembrane; LDL, low density lipoprotein; LRP1, LDL receptor related protein 1; APP, β-amyloid precursor protein; APLP1, APP-like protein 1.

YX'X'Z' (SEQ ID NO: 55)-type signals are found in endocytic receptors such as the transferrin receptor and the asialoglycoprotein receptor, intracellular sorting receptors such as the CI- and CD-MPRs, lysosomal membrane proteins such as LAMP-1 and LAMP-2, and TGN proteins such as TGN38 and furin, as well as in proteins localized to specialized endosomal-lysosomal organelles such as antigen-processing compartments (e.g., HLA-DM) and cytotoxic granules (e.g., GMP-17). The YX'X'Z' (SEQ ID NO: 55)-type signals are involved in the rapid internalization of proteins from the plasma membrane. However, their function is not limited to endocytosis, since the same motifs have been implicated in the targeting of transmembrane proteins to lysosomes and lysosome-related organelles.

Examples of YX'X'Z'(SEQ ID NO: 55)-type signals are provided in Table 3.

TABLE 3

YX'X'Z'-type signals

| Protein | Species | Sequence | |
|---|---|---|---|
| LAMP-1 | Human | Tm-RKRSHAGYQTI | SEQ ID NO: 87 |
| LAMP-2a | Human | Tm-KHHHAGYEQF | SEQ ID NO: 88 |
| LAMP-2a | Chicken | Tm-KKHHNTGYEQF | SEQ ID NO: 89 |
| LAMP-2b | Chicken | Tm-RRKSRTGYQSV | SEQ ID NO: 90 |
| LAMP-2c | Chicken | Tm-RRKSYAGYQTL | SEQ ID NO: 91 |
| LAMP | *Drosophila* | Tm-RRRSTSRGYMSF | SEQ ID NO: 92 |
| LAMP | Earthworm | Tm-RKRSRRGYEVM | SEQ ID NO: 93 |
| CD63 | Human | Tm-KSIRSGYEVM | SEQ ID NO: 94 |
| GMP-17 | Human | Tm-HCGGPRPGYETL | SEQ ID NO: 95 |
| GMP-17 | Mouse | Tm-HCRTRRAEYETL | SEQ ID NO: 96 |
| CD68 | Human | Tm-RRRPSAYQAL | SEQ ID NO: 97 |
| CD1b | Human | Tm-RRRSYQNIP | SEQ ID NO: 98 |
| CD1c | Human | Tm-KKHCSYQDIL | SEQ ID NO: 99 |
| CD1d | Mouse | Tm-RRRSAYQDIR | SEQ ID NO: 100 |
| CD1 | Rat | Tm-RKRRRSYQDIM | SEQ ID NO: 101 |
| Endolyn | Rat | Tm-KFCKSKERNYHTL | SEQ ID NO: 102 |
| Endolyn | *Drosophila* | Tm-KFYKARNERNYHTL | SEQ ID NO: 103 |
| TSC403 | Human | Tm-KIRLRCQSSGYQRI | SEQ ID NO: 104 |
| TSC403 | Mouse | Tm-KIRQRHQSSAYQRI | SEQ ID NO: 105 |
| Cystinosin | Human | Tm-HFCLYRKRPGYDQLN | SEQ ID NO: 106 |
| Putative solute carrier | Human | Tm-12-SLSRGSGYKEI | SEQ ID NO: 107 |

TABLE 3 -continued

YX'X'Z'-type signals

| Protein | Species | Sequence | | |
|---|---|---|---|---|
| TRP-2 | Human | Tm-RRLRKGYTPLMET-11 | SEQ ID NO: | 108 |
| HLA-DM ♦ | Human | Tm-RRAGHSSYTPLPGS-9 | SEQ ID NO: | 109 |
| LmpA | Dictyostelium | Tm-KKLRQQKQQGYQAIINNE | SEQ ID NO: | 110 |
| Putative lysosomal protein | Dictyostelium | Tm-RSKSNQNQSYNLIQL | SEQ ID NO: | 111 |
| LIMP-II | Dictyostelium | Tm-RKTFYNNNQYNGYNIIN | SEQ ID NO: | 112 |
| Transferrin receptor | Human | 16-PLSYTRFSLA-35-Tm | SEQ ID NO: | 113 |
| Asialoglycoprotein receptor H1 | Human | MTKEYQDLQHL-29-Tm | SEQ ID NO: | 114 |
| CI-MPR | Human | Tm-22-SYKYSKVNKE-132 | SEQ ID NO: | 115 |
| CD-MPR | Human | Tm-40-PAAYRGVGDD-16 | SEQ ID NO: | 116 |
| CTLA-4 | Human | Tm-10-TGVYVKMPPT-16 | SEQ ID NO: | 117 |
| Furin | Human | Tm-17-LISYKGLPPE-29 | SEQ ID NO: | 118 |
| TGN38 | Rat | Tm-23-ASDYQRLNLKL | SEQ ID NO: | 119 |
| gp41 | HIV-1 | Tm-13-RQGYSPLSFQT-144 | SEQ ID NO: | 120 |
| Acid phosphatase | Human | Tm-RMQAPPGYRH-VADGEDHA | SEQ ID NO: | 121 |

See legend to Table 1 for explanation of signal format

Dileucine-based sorting signals ([DE]X'X'X'LL[LI] (SEQ ID NO: 122)) play critical roles in the sorting of many type I, type II, and multispanning transmembrane proteins. Dileucine-based sorting signals are involved in rapid internalization and lysosomal degradation of transmembrane proteins and the targeting of proteins to the late endosomal-lysosomal compartments. Transmembrane proteins that contain constitutively active forms of this signal are mainly localised to the late endosomes and lysosomes.

Examples of [DE]X'X'X'LL[LI] (SEQ ID NO: 122) sorting signals are provided in Table 4.

TABLE 4

[DE]X'X'X'LL[LI] sorting signals

| Protein | Species | Signal | | |
|---|---|---|---|---|
| CD3-γ | Human | Tm-8-SDKQTLLPN-26 | SEQ ID NO: | 123 |
| LIMP-II | Rat | Tm-11-DERAPLIRT | SEQ ID NO: | 124 |
| Nmb | Human | Tm-37-QEKDPLLKN-7 | SEQ ID NO: | 125 |
| QNR-71 | Quail | Tm-37-TERNPLLKS-5 | SEQ ID NO: | 126 |
| Pmel17 | Human | Tm-33-GENSPLLSG-3 | SEQ ID NO: | 127 |
| Tyrosinase | Human | Tm-8-EEKQPLLME-12 | SEQ ID NO: | 128 |
| Tyrosinase | Medaka fish | Tm-16-GERQPLLQS-13 | SEQ ID NO: | 129 |
| Tyrosinase | Chicken | Tm-8-PEIQPLLTE-13 | SEQ ID NO: | 130 |
| TRP-1 | Goldfish | Tm-7-EGRQPLLGD-15 | SEQ ID NO: | 131 |
| TRP-1 | Human | Tm-7-EANQPLLTD-20 | SEQ ID NO: | 132 |
| TRP-1 | Chicken | Tm-7-ELHQPLLTD-20 | SEQ ID NO: | 133 |

TABLE 4 -continued

[DE|X'X'LL[LI] sorting signals

| Protein | Species | Signal | |
|---|---|---|---|
| TRP-2 | Zebrafish | Tm-5-REFEPLLNA-11 | SEQ ID NO: 134 |
| VMAT2 | Human | Tm-6-EEKMAILMD-29 | SEQ ID NO: 135 |
| TMAT1 | Human | Tm-6-EEKLAILSQ-32 | SEQ ID NO: 136 |
| VAchT | Mouse | Tm-10-SERDVLLDE-42 | SEQ ID NO: 137 |
| VAMP4 | Human | 19-SERRNLLED-88-Tm | SEQ ID NO: 138 |
| Neonatal FcR | Rat | Tm-16-DDSDGLLPG-19 | SEQ ID NO: 139 |
| CD4 | Human | Tm-12-SQIKRLLSE-17 | SEQ ID NO: 140 |
| CD4 | Cat | Tm-12-SHIKRLLSE-17 | SEQ ID NO: 141 |
| GLUT4 | Mouse | Tm-17-RRTPSLLEQ-17 | SEQ ID NO: 142 |
| GLUT4 | Human | Tm-17-HRTPSLLEQ-17 | SEQ ID NO: 143 |
| IRAP | Rat | 46-EPRGSRLLVR-53-Tm | SEQ ID NO: 144 |
| Ii | Human | MDDQRDLISNNEQLPMLGR-11-Tm | SEQ ID NO: 145 |
| Ii | Mouse | MDDQRDLISNHEQLPILGN-10-Tm | SEQ ID NO: 146 |
| Ii | Chicken | MAEEQRDLISSDGSSGVLPI-12-Tm | SEQ ID NO: 147 |
| Ii-1 | Zebrafish | MEPDHQNESLIQRVPSAETILGR-12-Tm | SEQ ID NO: 148 |
| Ii-2 | Zebrafish | MSSEGNETPLISDQSSVNMGPQP-8-Tm | SEQ ID NO: 149 |
| Lamp | Trypanosome | Tm-RPRRRTEEDELLPEEAEG-LIDPQN | SEQ ID NO: 150 |
| Menkes protein | Human | Tm-74-PDKHSLLVGDFREDDDTAL | SEQ ID NO: 151 |
| NPC1 | Human | Tm-13-TERERLLNP | SEQ ID NO: 152 |
| AQP4 | Human | Tm-32-VETDDLIL-29 | SEQ ID NO: 153 |
| RME-2 | C. elegans | Tm-104-FENDSLL | SEQ ID NO: 154 |
| Vam3p | S. cerevisiae | 153-NEQSPLLHN-121-Tm | SEQ ID NO: 155 |
| ALP | S. cerevisiae | 7-SEQTRLVP-18-Tm | SEQ ID NO: 156 |
| Gap1p | S. cerevisiae | Tm-23-EVDLDLLK-24 | SEQ ID NO: 157 |

See legend to Table 1 for explanation of signal format.

DX'X'LL signals constitute a distinct type of dileucine-based sorting signals. These signals are present in several transmembrane receptors and other proteins that cycle between the TGN and endosomes, such as the CI- and CD-MPRs, sortilin, the LDL-receptor-related proteins LRP3 and LRP10, and β-secretase.

Examples of DX'X'LL (SEQ ID NO: 158) sorting signals are provided in Table 5.

TABLE 5

DX'X'LL (SEQ ID NO: 158) sorting signals

| Protein | Species | Sequence | |
|---|---|---|---|
| CI-MPR | Human | Tm-151-SFHDDSDEDLLHI | SEQ ID NO: 159 |
| CI-MPR | Bovine | Tm-150-TFHDDSDEDLLHV | SEQ ID NO: 160 |
| CI-MPR | Rabbit | Tm-151-SFHDDSDEDLLNI | SEQ ID NO: 161 |

TABLE 5 -continued

DX'X'LL (SEQ ID NO: 158) sorting signals

| Protein | Species | Sequence | |
|---|---|---|---|
| CI-MPR | Chicken | Tm-148-SFHDDSDEDLLNV | SEQ ID NO: 162 |
| CD-MPR | Human | Tm-54-EESEERDDHLLPM | SEQ ID NO: 163 |
| CD-MPR | Chicken | Tm-54-DLSEERDDHLLPM | SEQ ID NO: 164 |
| Sortilin | Human | Tm-41-GYHDDSDEDLLE | SEQ ID NO: 165 |
| SorLA | Human | Tm-41-ITGFSDDVPMVIA | SEQ ID NO: 166 |
| Head-activator BP | Hydra | Tm-41-INRFSDDEPLVVA | SEQ ID NO: 167 |
| LRP3 | Human | Tm-237-MLEASDDEALLVC | SEQ ID NO: 168 |
| ST7 | Human | Tm-330-KNETSDDEALLLC | SEQ ID NO: 169 |
| LRP10 | Mouse | Tm-235-WVVEAEDEPLLA | SEQ ID NO: 170 |
| LRP10 | Human | Tm-237-WVAEAEDEPLLT | SEQ ID NO: 171 |
| Bela-secretase | Human | Tm-9-HDDFADDISLLK | SEQ ID NO: 172 |
| Mucolipin-1 | Mouse | Tm-43-GRDSPEDHSLLVN | SEQ ID NO: 173 |
| Nonclassical MHC-I | Deer mouse | Tm-6-VRCHPEDDRLLG | SEQ ID NO: 174 |
| FLJ30532 | Human | Tm-83-HRVSQDDLDLLTS | SEQ ID NO: 175 |
| GGA1 | Human | 350-ASVSLLDDELMSL-275 | SEQ ID NO: 176 |
| GGA1 | Human | 415-ASSGLDDLDLLGK-211 | SEQ ID NO: 177 |
| GGA2 | Human | 408-VQNPSADRNLLDL-192 | SEQ ID NO: 178 |
| GGA3 | Human | 384-NALSWLDEELLCL-326 | SEQ ID NO: 179 |
| GGA | Drosophila | 447-TVDSIDDVPLLSD-116 | SEQ ID NO: 180 |

See legend to Table 1 for exsplanation of signal format.
Serine and threonine residues are underlined.

Another family of sorting motifs is provided by clusters of acidic residues containing sites for phosphorylation by CKII. This type of motif is often found in transmembrane proteins that are localized to the TGN at steady state, including the prohormone-processing enzymes furin, PC6B, PC7, CPD, and PAM, and the glycoprotein E of herpes virus 3.

Examples of acidic cluster signals are provided in Table 6.

TABLE 6

Acidic cluster sorting signals

| Protein | Species | Sequence | |
|---|---|---|---|
| Furin | Mouse | Tm-31-QEECPSDSEEDEG-14 | SEQ ID NO: 181 |
| PC6B (1)$^a$ | Mouse | Tm-39-RDRDYDEDDEDDI-36 | SEQ ID NO: 182 |
| PC6B (2) | Mouse | Tm-69-LDETEDDELEYDDES-4 | SEQ ID NO: 183 |
| PC7 | Human | Tm-38-KDPDEVETES-47 | SEQ ID NO: 184 |
| CPD | Human | TM-36-HEFQDETDTEEET-6 | SEQ ID NO: 185 |
| PAM | Human | Tm-59-QEKEDDGSESEEEY-12 | SEQ ID NO: 186 |
| VMAT2 | Human | Tm-35-GEDEESESD | SEQ ID NO: 187 |
| VMAT1 | Human | Tm-35-GEDSDEEPDHEE | SEQ ID NO: 188 |
| VAMP4 | Human | 25-LEDDSDEEEDF-81-Tm | SEQ ID NO: 189 |

TABLE 6 -continued

Acidic cluster sorting signals

| Protein | Species | Sequence | |
|---|---|---|---|
| Glycopro-tein B | HCMV | Tm-125-KD<u>S</u>DEEENV | SEQ ID NO: 190 |
| Glycopro-tein E | Herpes virus 3 | Tm-28-FED<u>S</u>E<u>ST</u>D<u>T</u>EEEF-21 | SEQ ID NO: 191 |
| Nef | HIV-I (AAL65476) | 55-LEAQEEEV-139 | SEQ ID NO: 192 |
| Kex1p (1) | S. cerevisiae | Tm-29-ADDLE<u>S</u>GLGAEDDLE QDEQLEG-40 | SEQ ID NO: 193 |
| Kex1p (2) | S. cerevisiae | Tm-79-<u>T</u>EIDE<u>S</u>EMTDF | SEQ ID NO: 194 |
| Kex2p | S. cerevisiae | Tm-36-<u>T</u>EPEEVEDFDFDL<u>S</u>EDH-61 | SEQ ID NO: 195 |
| Vps10p | S. cerevisiae | Tm-112-FEIEEDDVP<u>TL</u>EEEH-37 | SEQ ID NO: 196 |

See legend to Table 1 for explanation of signal format Serine and threonine residues are underlined.
<sup>a</sup>The number in parentheses is the motif number.

The KDEL (SEQ ID NO: 51) receptor binds protein in the ER-Golgi intermediate compartment, or in the early Golgi and returns them to the ER. Although the common mammalian signal is KDEL (SEQ ID NO: 51), it has been shown that the KDEL(SEQ ID NO: 51) receptor binds the sequence HDEL (SEQ ID NO: 194) more tightly (Scheel et al; J. Biol. Chem. 268; 7465 (1993)). The intracellular retention signal may be HDEL (SEQ ID NO: 197).

KKX'X' (SEQ ID NO: 52) and KX'KX'X' (SEQ ID NO: 53) signals are retrieval signals which can be placed on the cytoplasmic side of a type I membrane protein. Sequence requirements of these signals are provided in detail by Teasdale & Jackson (Annu. Rev. Cell Dev. Biol.; 12; 27 (1996)).

The intracellular retention signal may be selected from the group of: NPX'Y (SEQ ID NO: 54), YX'X'Z (SEQ ID NO: 55), [DE]X'X'X'L[LI] (SEQ ID NO: 56), DX'X'LL (SEQ ID NO: 57), DP[FW] (SEQ ID NO: 58), FX'DX'F(SEQ ID NO: 59), NPF, LZX'Z[DE] (SEQ ID NO: 60), LLDLL (SEQ ID NO: 61), PWDLW (SEQ ID NO: 52), KDEL (SEQ ID NO: 51), HDEL (SEQ ID NO: 197), KKX'X' (SEQ ID NO: 52) or KX'KX'X' (SEQ ID NO: 53); wherein X' is any amino acid and Z' is an amino acid with a bulky hydrophobic side chain.

The intracellular retention signal may be any sequence shown in Tables 2 to 6.

The intracellular retention signal may comprise the Tyrosinase-related protein (TYRP)-1 intracellular retention signal. The intracellular retention signal may comprise the TYRP-1 intracellular domain. The intracellular retention signal may comprise the sequence NQPLLTD (SEQ ID NO: 35).

TYRP1 is a well-characterized melansomal protein which is retained in the melanosome (a specialized lysosome) at >99% efficiency. TYRP1 is a 537 amino acid transmembrane protein with a lumenal domain (1-477aa), a transmembrane domain (478-501), and a cytoplasmic domain (502-537). A di-leucine signal residing on the cytoplasmic domain causes retention of the protein. This di-leucine signal has the sequence shown as SEQ ID NO: 35 (NQPLLTD).

The intracellular retention signal may be in the endodomain of the transmembrane protein. In other words, the intracellular retention signal may be in the domain of the transmembrane protein which would be on the intracellular side of the cell membrane if the protein was correctly expressed at the cell surface.

The endodomain of the transmembrane protein may comprise at least 100, at least 150, at least 200, at least 300 or at least 500 amino acids.

The endodomain comprising the intracellular retention signal may be located at the carboxy terminus of the transmembrane protein. In particular, where the transmembrane protein comprises a signal sequence at the amino terminus of the peptide the endodomain comprising the intracellular retention signal may be located at the carboxy terminus.

The intracellular retention signal may be proximal to the transmembrane domain, for instance being immediately connected to it. The intracellular retention signal may be distal to the transmembrane domain—for instance at the carboxy-terminus of the endodomain. The positioning of the retention signal modulates its activity allowing "tuning" of the relative expression of two proteins. For instance in the case of the TYRP1 di-leucine motif, proximal placement results in low-level surface expression, while distal placement results in intermediate surface expression, as shown in the Examples.

Polypeptide of Interest

Any or all of A or B; or A, B or C of the nucleic acid sequences in the constructs defined herein may encode a transmembrane protein comprising an intracellular retention signal.

The other nucleic acid sequence may encode any polypeptide of interest (POI). For example, the other POI may be an intracellular protein such as a nucleic protein, a cytoplasmic protein or a protein localised to a membrane-bound compartment; a secretory protein or a transmembrane protein.

Any or all of A or B; or A, B or C of the nucleic acid sequences in the constructs defined herein may encode a chimeric antigen receptor (CAR). The nucleic acid constructs described in the Examples encode two chimeric antigen receptors.

The nucleic acid constructs described in the Examples encode the following polyproteins which comprise the various components in the order they are listed:

1. Polyprotein Comprising Anti-CD19 CAR and Anti-CD33 CAR with Proximal Tyrp-1 Retention on the Anti-CD19 CAR Signal peptide derived from Human CD8a:
(SEQ ID No. 38)
MSLPVTALLLPLALLLHAARP scFv aCD19:
(SEQ ID No. 39)
DIQMTQTTSSLSASLGDRVTISCRASQDISKYLNVVYQQKPDGTVKLLIYHTSRLHSGVPSRF

SGSGSGTDYSLTISNLEQEDIATYFCQQGNTLPYTFGGGTKLEITKAGGGGSGGGGSGGG

GSGGGGSEVKLQESGPGLVAPSQSLSVTCTVSGVSLPDYGVSWIRQPPRKGLEWLGVIW

GSETTYYNSALKSRLTIIKDNSKSQVFLKMNSLQTDDTAIYYCAKHYYYGGSYAM DYWGQG

TSVTVS

Linker:
SD

Human CD8aSTK:
(SEQ ID No. 40)
PITTPAPRPPTPAPTIASQPLSLRPEACRPAAGGAVHTRGLDFACDI

Human CD28TM:
(SEQ ID No. 41)
FWVLVVVGGVLACYSLLVTVAFIIFWV

Human Typr-1 intracellular domain (retention signal):
(SEQ ID No. 42)
RARRSMDEANQPLLTDQYQCYAEEYEKLQNPNQSVV Human CD3zeta intracellular domain:
(SEQ ID No. 43)
RRVKFSRSADAPAYQQGQNQLYNELNLGRREEYDVLDKRRGRDPEMGGKPRRKNPQEG

LYNELQKDKMAEAYSEIGMKGERRRGKGHDGLYQGLSTATKDTYDALHMQALPPR 2A peptide:
(SEQ ID No. 24)
RAEGRGSLLTCGDVEENPGP Signal peptide derived from mouse Ig kappa:
(SEQ ID No. 44)
MAVPTQVLGLLLLWLTDA scFv aCD33:
(SEQ ID No. 45)
RCDIQMTQSPSSLSASVGDRVTITCRASEDIYFNLVWYQQKPGKAPKWYDTNRLADGVPS

RFSGSGSGTQYTLTISSLQPEDFATYYCQHYKNYPLTFGQGTKLEIKRSGGGGSGGGGSG

GGSGGGGSRSEVQLVESGGGLVQPGGSLRLSCAASGFTLSNYGMHWIRQAPGKGLEW

VSSISLNGGSTYYRDSVKGRFTISRDNAKSTLYLQMNSLRAEDTAVYYCAAQDAYTGGYFD

YWGQGTLVTVSSM

Linker:
DPA

Hinge and Fc derived from human IgG1 with mutations to prevent FcRg association (HCH2CH3pvaa):
(SEQ ID No. 46)
EPKSPDKTHTCPPCPAPPVAGPSVFLFPPKPKDTLMIARTPEVTCVVVDVSHEDPEVKFNW

YVDGVEVHNAKTKPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK

```
Linker:
                                                   (SEQ ID No. 47)
KDPK Human CD148TM:
                                                   (SEQ ID No. 48)
AVFGCIFGALVIVTVGGFIFW Human CD148 intracellular domain:
                                                   (SEQ ID No. 49)
RKKRKDAKNNEVSFSQIKPKKSKLIRVENFEAYFKKQQADSNCGFAEEYEDLKLVGISQPKY

AAELAENRGKNRYNNVLPYDISRVKLSVQTHSTDDYINANYMPGYHSKKDFIATQGPLPNTL

KDFWRMVWEKNVYAIIMLTKCVEQGRTKCEEYWPSKQAQDYGDITVAMTSEIVLPEVVTIRD

FTVKNIQTSESHPLRQFHFTSWPDHGVPDTTDLLINFRYLVRDYMKQSPPESPILVHCSAGV

GRTGTFIAIDRLIYQIENENTVDVYGIVYDLRMHRPLMVQTEDQYVFLNQCVLDIVRSQKDSK

VDLIYQNTTAMTIYENLAPVTTFGKTNGYIA
```

2. Polyprotein Comprising Anti-CD19 CAR and Anti-CD33 CAR with Distal Tyrp-1 Retention on the Anti-CD19 CAR

```
Signal peptide derived from Human CD8a:
                                                   (SEQ ID No. 38)
MSLPVTALLLPLALLLHAARP scFv aCD19:
                                                   (SEQ ID No. 39)
DIQMTQTTSSLSASLGDRVTISCRASQDISKYLNWYQQKPDGTVKLLIYHTSRLHSGVPSRF

SGSGSGTDYSLTISNLEQEDIATYFCQQGNTLPYTFGGGTKLEITKAGGGGSGGGGSGGG

GSGGGGSEVKLQESGPGLVAPSQSLSVTCTVSGVSLPDYGVSWIRQPPRKGLEWLGVIW

GSETTYYNSALKSRLTIIKDNSKSQVFLKMNSLQTDDTAIYYCAKHYYYGGSYAMDYWGQG

TSVTVS

Linker:
SD

Human CD8aSTK:
                                                   (SEQ ID No. 40)
PITTPAPRPPTPAPTIASQPLSLRPEACRPAAGGAVHTRGLDFACDI Human CD28TM:
                                                   (SEQ ID No. 41)
FWVLVVVGGVLACYSLLVTVAFIIFWV Human CD3zeta intracellular domain:
                                                   (SEQ ID No. 43)
RRVKFSRSADAPAYQQGQNQLYNELNLGRREEYDVLDKRRGRDPEMGGKPRRKNPQEG

LYNELQKDKMAEAYSEIGMKGERRRGKGHDGLYQGLSTATKDTYDALHMQALPPR

Human Typr-1 intracellular domain (retention signal):
                                                   (SEQ ID No. 42)
RARRSMDEANQPLLTDQYQCYAEEYEKLQNPNQSVV 2A peptide:
                                                   (SEQ ID No. 24)
RAEGRGSLLTCGDVEENPGP Signal peptide derived from mouse Ig kappa:
                                                   (SEQ ID No. 44)
MAVPTQVLGLLLLWLTDA scFv aCD33:
                                                   (SEQ ID No. 45)
RCDIQMTQSPSSLSASVGDRVTITCRASEDIYFNLVWYQQKPGKAPKWYDTNRLADGVPS

RFSGSGSGTQYTLTISSLQPEDFATYYCQHYKNYPLTFGQGTKLEIKRSGGGGSGGGGSG

GGGSGGGGSRSEVQLVESGGGLVQPGGSLRLSCAASGFTLSNYGMHWIRQAPGKGLEW
```

-continued

VSSISLNGGSTYYRDSVKGRFTISRDNAKSTLYLQMNSLRAEDTAVYYCAAQDAYTGGYFD

YWGQGTLVTVSSM

Linker:
DPA

Hinge and Fc derived from human IgG1 with mutations to prevent
FcRg association (HCH2CH3pvaa):
(SEQ ID No. 46)
EPKSPDKTHTCPPCPAPPVAGPSVFLFPPKPKDTLMIARTPEVTCVVVDVSHEDPEVKFNW

YVDGVEVHNAKTKPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK

Linker:
(SEQ ID No. 47)
KDPK

Human CD148TM:
(SEQ ID No. 48)
AVFGCIFGALVIVTVGGFIFW

Human CD148 intracellular domain:
(SEQ ID No. 49)
RKKRKDAKNNEVSFSQIKPKKSKLIRVENFEAYFKKQQADSNCGFAEEYEDLKLVGISQPKY

AAELAENRGKNRYNNVLPYDISRVKLSVQTHSTDDYINANYMPGYHSKKDFIATQGPLPNTL

KDFWRMVWEKNVYAIIMLTKCVEQGRTKCEEYWPSKQAQDYGDITVAMTSEIVLPEVVTIRD

FTVKNIQTSESHPLRQFHFTSWPDHGVPDTTDLLINFRYLVRDYMKQSPPESPILVHCSAGV

GRTGTFIAIDRLIYQIENENTVDVYGIVYDLRMHRPLMVQTEDQYVFLNQCVLDIVRSQKDSK

VDLIYQNTTAMTIYENLAPVTTFGKTNGYIA

3. Polyprotein Comprising Anti-CD19 CAR and Anti-CD33
CAR with E3/19K Retention on the Anti-CD33 CAR Signal peptide derived from Human CD8a:
(SEQ ID No. 38)
MSLPVTALLLPLALLLHAARP scFv aCD19:
(SEQ ID No. 39)
DIQMTQTTSSLSASLGDRVTISCRASQDISKYLNWYQQKPDGTVKLLIYHTSRLHSGVPSRF

SGSGSGTDYSLTISNLEQEDIATYFCQQGNTLPYTFGGGTKLEITKAGGGGSGGGGSGGG

GSGGGGSEVKLQESGPGLVAPSQSLSVTCTVSGVSLPDYGVSWIRQPPRKGLEWLGVIW

GSETTYYNSALKSRLTIIKDNSKSQVFLKMNSLQTDDTAIYYCAKHYYYGGSYAMDYWGQG

TSVTVS

Linker:
SD

Human CD8aSTK:
(SEQ ID No. 40)
PITTPAPRPPTPAPTIASQPLSLRPEACRPAAGGAVHTRGLDFACDI

Human CD28TM:
(SEQ ID No. 41)
FWVLVVVGGVLACYSLLVTVAFIIFWV

Human CD3zeta intracellular domain:
(SEQ ID No. 43)
RRVKFSRSADAPAYQQGQNQLYNELNLGRREEYDVLDKRRGRDPEMGGKPRRKNPQEG

LYNELQKDKMAEAYSEIGMKGERRRGKGHDGLYQGLSTATKDTYDALHMQALPPR

-continued 2A peptide:
(SEQ ID No. 24)
RAEGRGSLLTCGDVEENPGP

Signal peptide derived from mouse Ig kappa:
(SEQ ID No. 44)
MAVPTQVLGLLLLWLTDA scFv aCD33:
(SEQ ID No. 45)
RCDIQMTQSPSSLSASVGDRVTITCRASEDIYFNLVWYQQKPGKAPKWYDTNRLADGVPS

RFSGSGSGTQYTLTISSLQPEDFATYYCQHYKNYPLTFGQGTKLEIKRSGGGGSGGGGSG

GGGSGGGGSRSEVQLVESGGGLVQPGGSLRLSCAASGFTLSNYGMHWIRQAPGKGLEW

VSSISLNGGSTYYRDSVKGRFTISRDNAKSTLYLQMNSLRAEDTAVYYCAAQDAYTGGYFD

YWGQGTLVTVSSM

Linker:
DPA

Hinge and Fc derived from human IgG1 with mutations to prevent
FcRg association (HCH2CH3pvaa):
(SEQ ID No. 46)
EPKSPDKTHTCPPCPAPPVAGPSVFLFPPKPKDTLMIARTPEVTCVVVDVSHEDPEVKFNW

YVDGVEVHNAKTKPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK

Linker:
(SEQ ID No. 47)
KDPK

Human CD148TM:
(SEQ ID No. 48)
AVFGCIFGALVIVTVGGFIFW

Human CD148 intracellular domain:
(SEQ ID No. 49)
RKKRKDAKNNEVSFSQIKPKKSKLIRVENFEAYFKKQQADSNCGFAEEYEDLKLVGISQPKY

AAELAENRGKNRYNNVLPYDISRVKLSVQTHSTDDYINANYMPGYHSKKDFIATQGPLPNTL

KDFWRMVWEKNVYAIIMLTKCVEQGRTKCEEYWPSKQAQDYGDITVAMTSEIVLPEVVTIRD

FTVKNIQTSESHPLRQFHFTSWPDHGVPDTTDLLINFRYLVRDYMKQSPPESPILVHCSAGV

GRTGTFIAIDRLIYQIENENTVDVYGIVYDLRMHRPLMVQTEDQYVFLNQCVLDIVRSQKDSK

VDLIYQNTTAMTIYENLAPVTTFGKTNGYIA

Adenoviral E3/19K cytosolic tail:
(SEQ ID No. 36)
KYKSRRSFIDEKKMP

In the above Polyprotein 3, the E3/19K cytosolic tail may be replaced with a truncated version having the sequence: DEKKMP (SEQ ID NO: 37)

As shown in the Examples, it was found that, for the tyrp-1 retention signal, low levels of expression could be achieved by placing the retention signal between "Human CD28TM" and "Human CD3zeta intracellular domain" in the sequence given above, whereas medium levels of expression could be achieved by placing the retention signal between "Human CD3zeta intracellular domain" and "2A peptide".

The E3/19K retention signal caused reduction in expression of the anti-CD33 CAR when placed at the C-terminus of the anti-CD33 CAR.

Vector

The present invention also provides a vector comprising a nucleic acid construct according to the first aspect of the invention.

Such a vector may be used to introduce the nucleic acid construct into a host cell so that it expresses the first and second polypeptide.

The vector may, for example, be a plasmid or a viral vector, such as a retroviral vector or a lentiviral vector, or a transposon based vector or synthetic mRNA.

The vector may be capable of transfecting or transducing a mammalian cell, for example a T cell.

Cell

The present invention furthers provides a cell comprising a nucleic acid construct or vector of the present invention which expresses the first and second polypeptide encoded by the nucleic acid sequence.

The cell may be any eukaryotic cell capable of expressing a transmembrane protein at the cell surface, such as an immunological cell.

Protein

The present invention also provides a transmembrane protein comprising an extracellular domain, a transmembrane domain and an endodomain wherein the endodomain comprises an exogenous intracellular retention signal as defined herein.

'Exogenous' means that the intracellular retention signal is not part of the wild type sequence of the transmembrane protein. Wild type sequence refers to the amino acid sequence of the protein which commonly occurs in nature.

The present inventors have demonstrated that the inclusion of an exogenous intracellular retention signal in the endodomain of a transmembrane protein causes the transmembrane protein to be directed to an intracellular compartment. As such the amount of the transmembrane protein expressed at the cell surface is reduced compared to an equivalent transmembrane protein which does not include an intracellular retention signal in the transmembrane domain.

Method

In a further aspect the present invention relates to a method for modulating the relative cell surface expression of a transmembrane protein expressed from a single nucleic acid construct as a polyprotein with a second protein; by including an intracellular retention signal in the nucleic acid sequence which encodes the transmembrane protein.

The invention will now be further described by way of Examples, which are meant to serve to assist one of ordinary skill in the art in carrying out the invention and are not intended in any way to limit the scope of the invention.

EXAMPLES

Example 1—Dissection of TYRP1 Lysozomal Retention Signals

Figure 1:
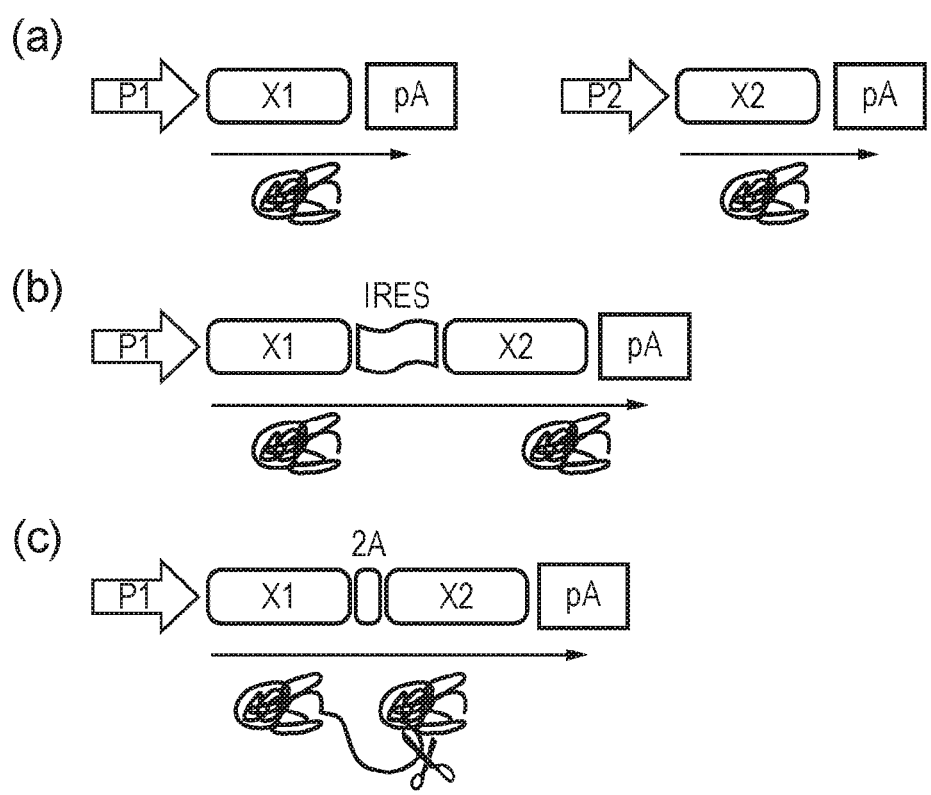
FIG. 1: Methods utilised to express different proteins from the same vector
(a) Two different promoters within the same cassette result in two different transcripts which each give rise to separate proteins. (b) Use of an Internal Ribosome Entry sequence (IRES) leads to a single transcript which is translated into two separate proteins. (c) Use of the FMDV 2A peptide results in a single transcript, and a single polyprotein which rapidly cleaves into two separate proteins.
Figure 2:
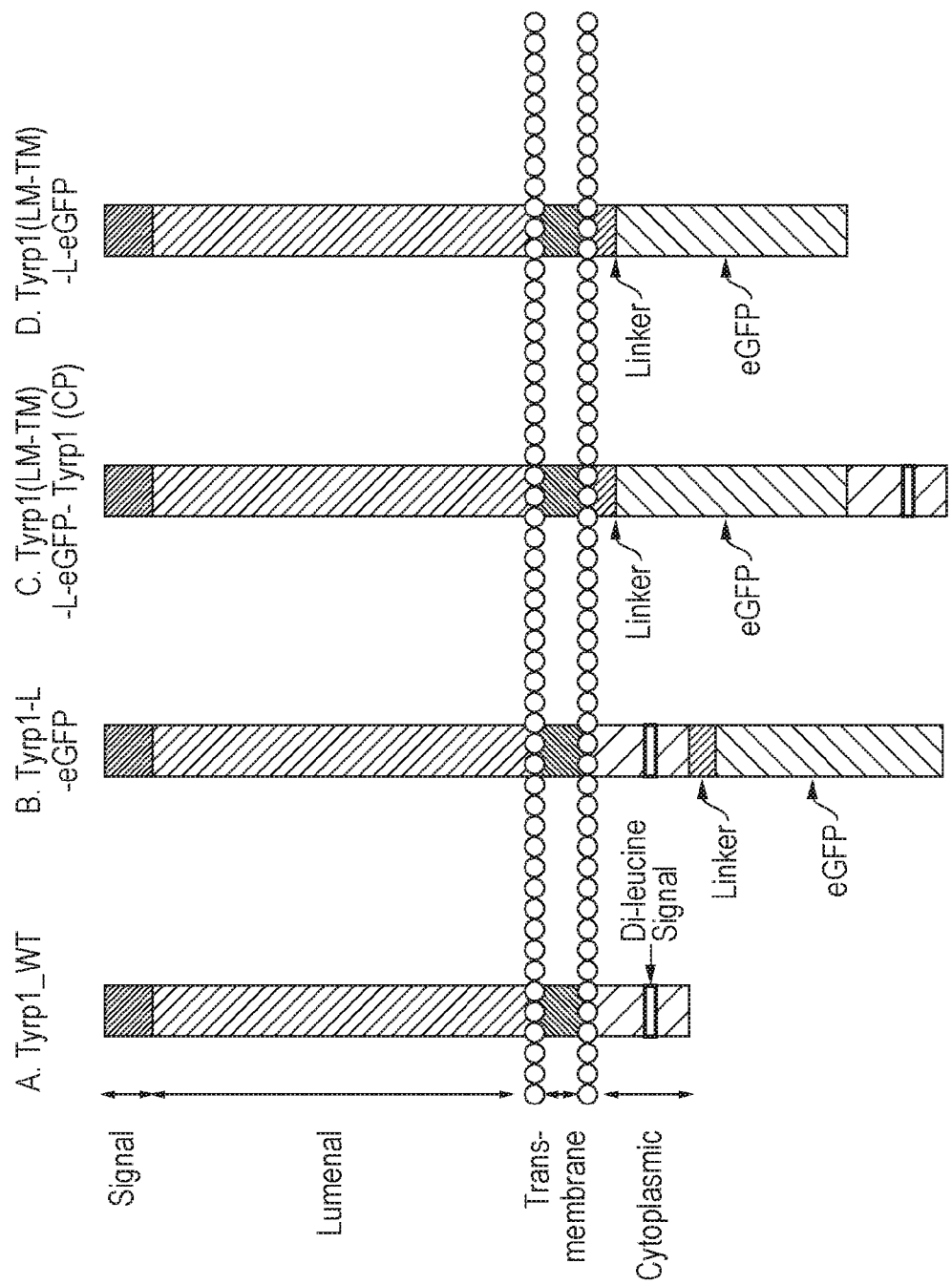
FIG. 2: TYRP1 endodomain is able to direct the retention of a transmembrane protein with a complex endodomain
Tyrp1 is a type I transmembrane protein, 537aa long. The di-leucine motif, which retains the protein in the intracellular compartment, is indicated as a black rectangle on the cytoplasmic domain. (A) Tyrp1 (wt). Wild type Tyrp1 consists of a peptide signal, a luminal domain, a transmembrane domain, and a cytoplasmic domain. The cytoplasmic domain contains the di-leucine retention signal. (B) Tyrp1 (wt)-SG Linker-eGFP. This construct contains the wild type Tyrp1 simply fused to eGFP via a serine-glycine-glycine-glycine-serine linker. The Tyrp1-L-eGFP represents the cytoplasmic-proximal Tyrp1. (C) Tyrp1 Lumenal (LM)-Transmembrane (TM)-SG Linker-eGFP-Tyrp1 Cytoplasmic (CP). This construct constitutes the cytoplasmic-distal Tyrp1, since SG linker-eGFP interposes between the transmembrane and cytoplasmic domains. D: Tyrp1 Lumenal (LM)-Transmembrane (TM)-SG Linker-eGFP. This construct serves as the positive control, as the cytoplasmic domain containing the retention signal has been excluded. All constructs are co-expressed with IRES.CD34. Staining of transduced SupT1 cells is shown with intracellular and surface staining bottom left/right respectively.
Figure 2:
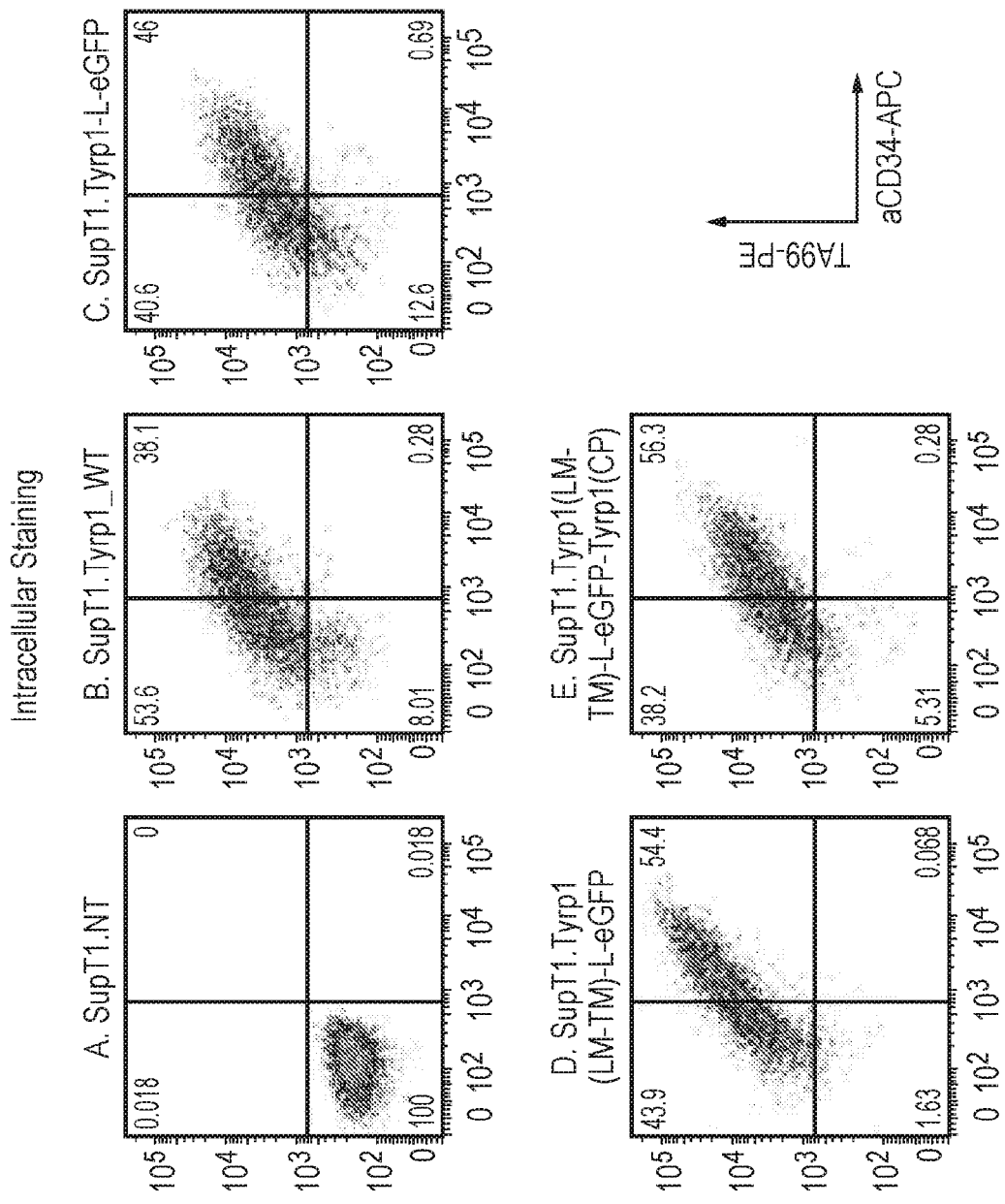
Figure 2:
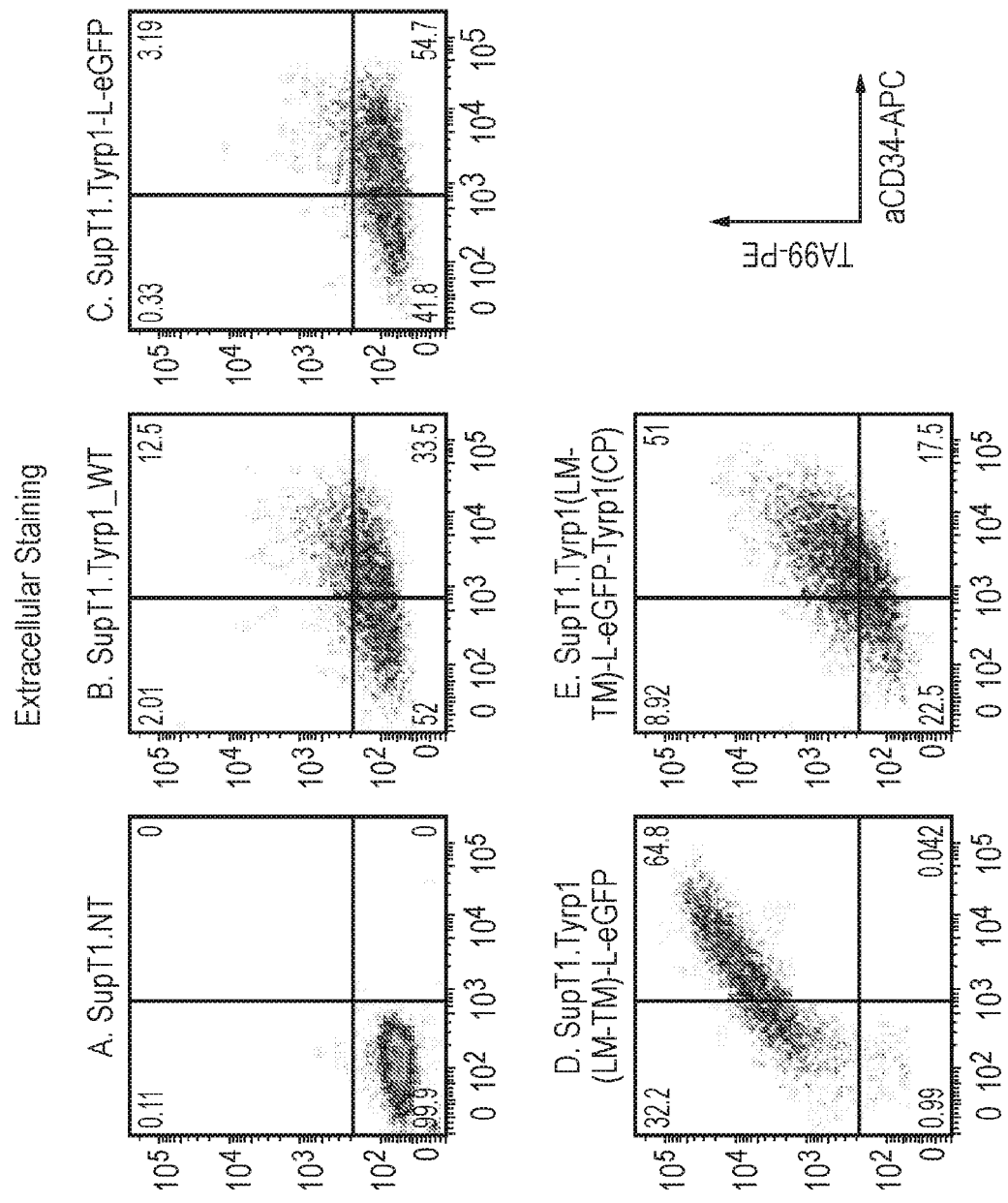

The ability of the Tyrosinase-related protein 1 (TYRP1) retention signal to cause retention of a polypeptide when in the context of a more complex endodomain was determined using a number of constructs (FIG. 2). The wild-type construct was compared with constructs where enhanced Green Fluorescent Protein (eGFP) was added or replaced the TYRP1 endodomain. Where eGFP was added, it was placed either after or before the native endodomain so the retention signal was either in its native location (just under the membrane), or distal to it.

All constructs are co-expressed with IRES.CD34. Staining of transduced SupT1 cells is shown with intracellular and surface staining in FIG. 2.

It was found that replacement of the endodomain resulted in very bright surface expression, introduction of eGFP after the retention signal to almost no surface expression and introduction before the retention signal to intermediate surface expression (FIG. 2).

Example 2—Modulation of the Relative Expression of a Transmembrane Protein Co-Expressed from a Single Expression Cassette with a Separate Protein An expression cassette encoding two CAR transmembrane proteins was modified such that one of the CAR proteins had the lysozomal retention signal from TYRP1 introduced either proximal or distal to the membrane. Expression of each of these two new variants at the cell surface was compared with that of the original unmodified CAR protein.

PBMCs were isolated from blood and stimulated using PHA and IL-2. Two days later the cells were transduced on retronectin coated plates with retro virus containing the CD19:CD33 CAR construct. On day 5 the expression level of the two CARs translated by the construct was evaluated via flow cytometry and the cells were depleted of CD56+ cells (predominantly NK cells). On day 6 the PBMCs were placed in a co-culture with target cells at a 1:2 effector to target cell ratio. On day 8 the supernatant was collected and analysed for IFN-gamma secretion via ELISA.

Figure 3:
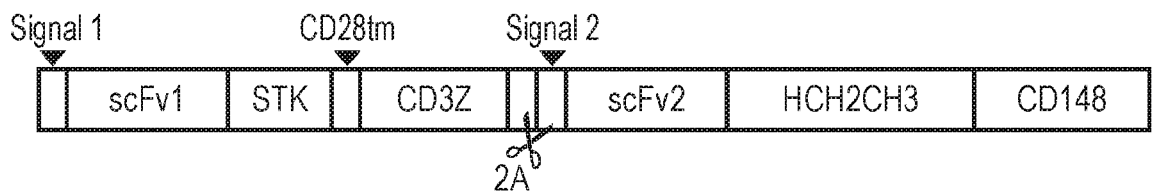
FIG. 3: Functionality of the TYRP1 retention signal in primary cells
Figure 3:
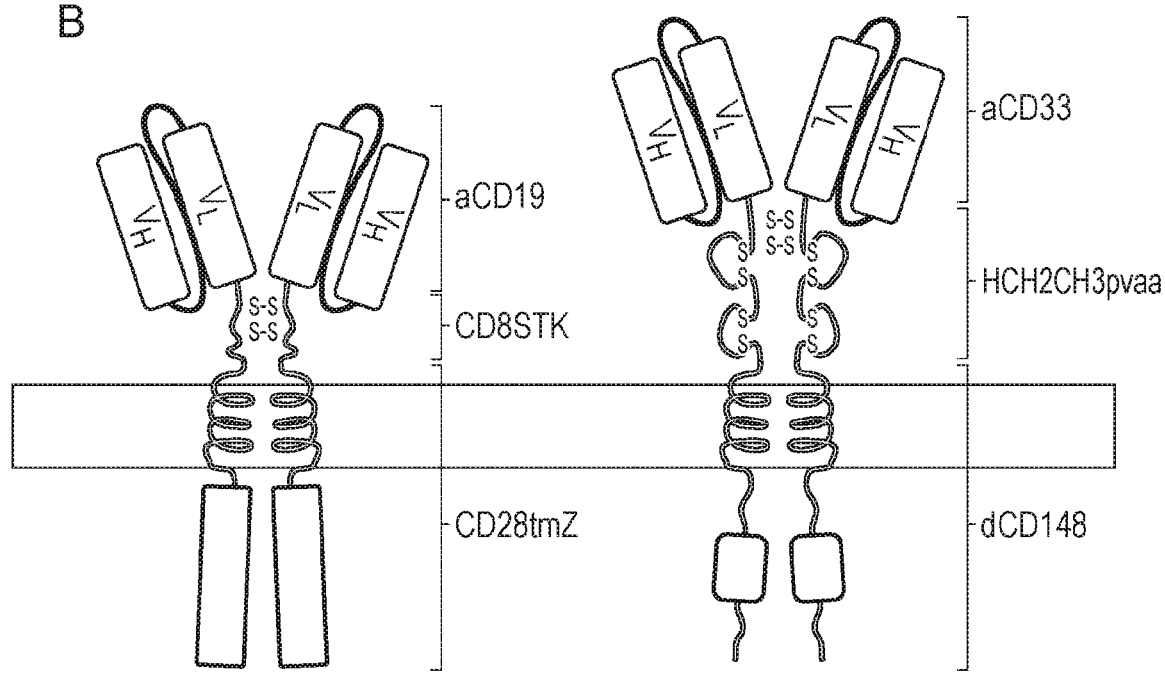
Figure 3:
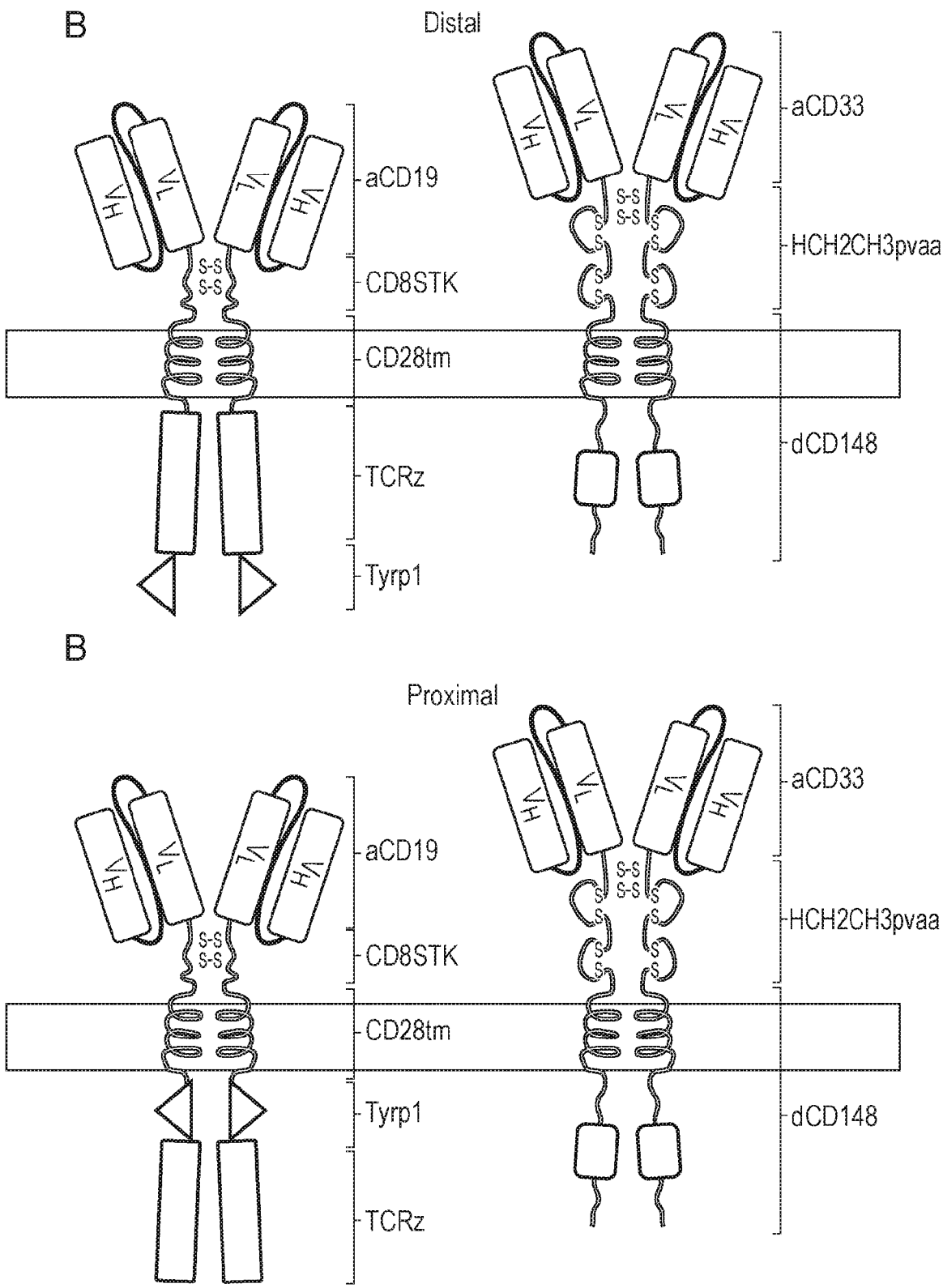
Figure 3:
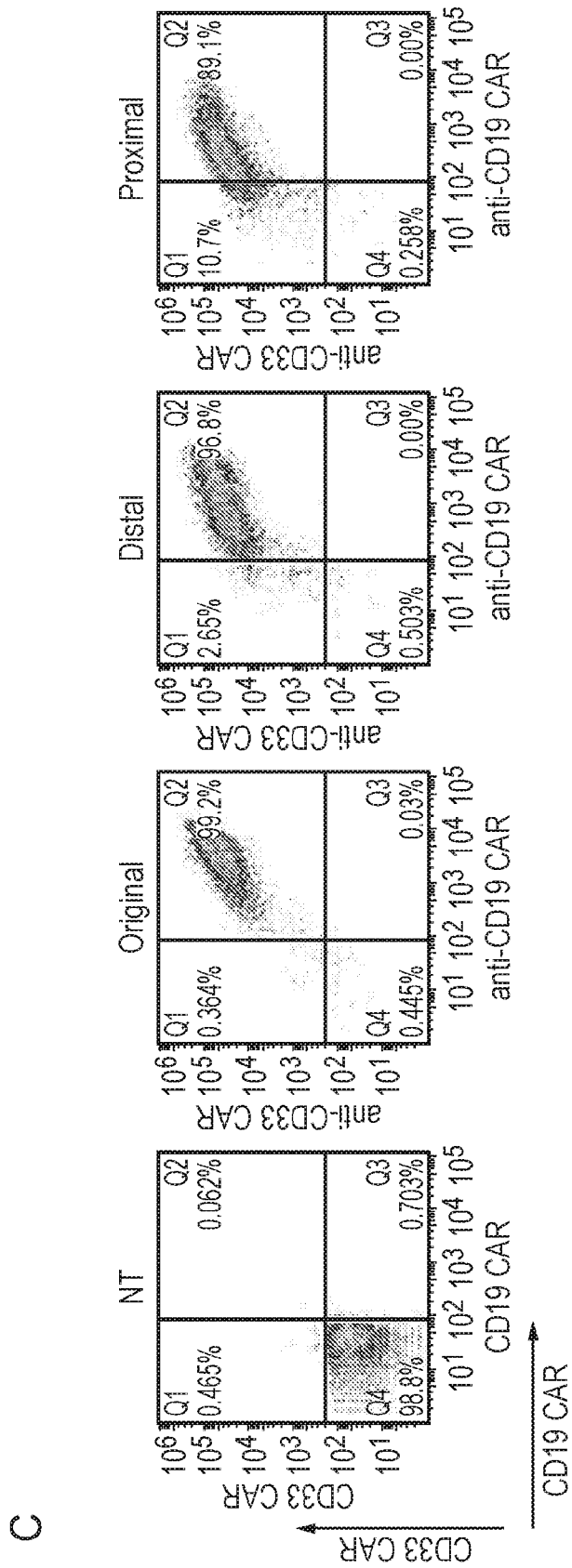

The pattern observed with Tyrp1-eGFP fusions was observed with some reduction of expression of modified transmembrane protein with the distal retention signal and marked reduction in the case of proximal retention signal. As expected, expression of the second transmembrane protein from the cassette was not altered (FIG. 3).

Example 3—Modulation of Expression Using a Retention Signal from the Adenoviral E3/19K Protein The human adenovirus E3/19K protein is a type I transmembrane glycoprotein of the Endoplasmic Reticulum/Golgi that abrogates cell surface transport of major histocompatibility complex class I (MHC-I) and MHC-I-related chain A and B (MICA/B) molecules. The retention motif was identified to be depended on the cytosolic tail of the adenovirus E3/19K protein. More specifically, the last 6aa DEKKMP (SEQ ID NO: 37) was found to be the most important for retention. The optimal positioning was found to be at the c-terminus of the protein.

An expression cassette encoding two CAR transmembrane proteins, as described in Example 2, was modified such that one of the CAR proteins had the retention motif from adenovirus E3/19K protein. In this experiment, the retention motif on the second CAR in the expression cassette (the anti-CD33 inhibitory CAR).

Figure 5:
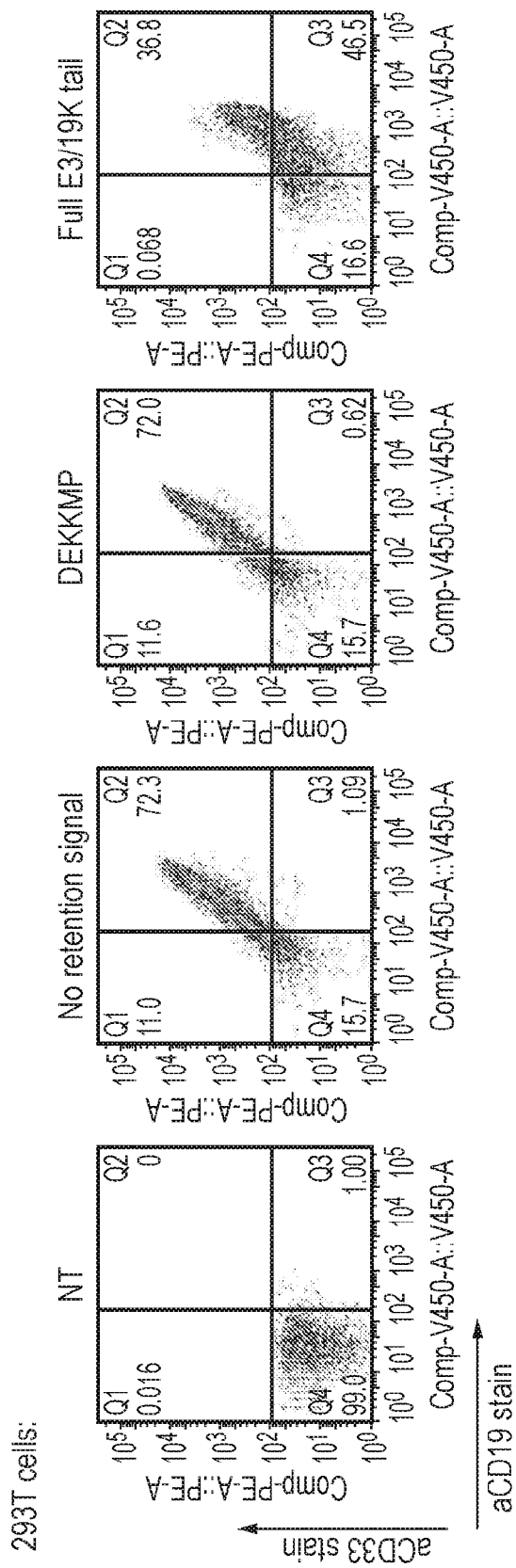
Figure 5:
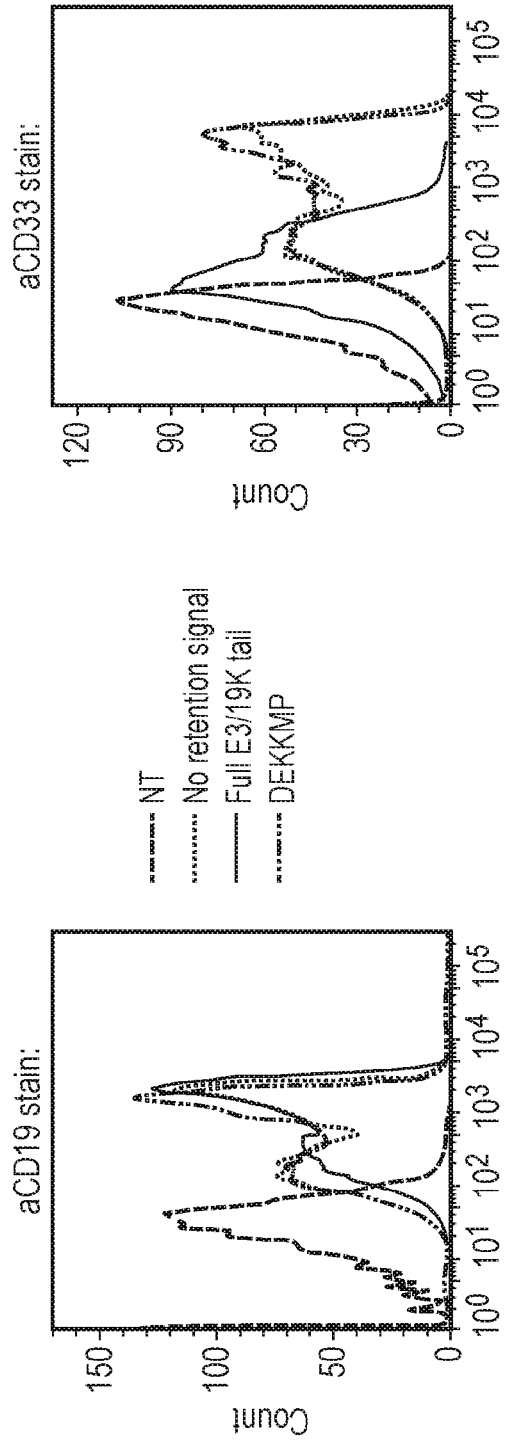

Constructs were generated comprising either the entire cytosolic tail of adenovirus E3/19K protein or only the last 6aa from E3/19K (DEKKMP (SEQ ID NO: 37)), which were found to be critical for its Golgi/ER retention ability (FIG. 4). These constructs were transfected into 293T cells and stained primarily with a chimeric soluble CD19-Rabbit Fc and a chimeric soluble CD33-Mouse Fc proteins. These cells were then subsequently stained with an anti-Rabbit Fc-FITC and an anti-Mouse Fc-APC (FIG. 5). These cells show a clear retention when the full length adenovirus E3/19K protein, or the DEKKMP (SEQ ID NO: 37) motif, was placed on the anti-CD33 receptor but had no effect on anti-CD19 receptor expression levels.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cell biology or related fields are intended to be within the scope of the following claims.

The invention claimed is:

1. A nucleic acid construct comprising the following structure:

A-X-B in which (a) A comprises a nucleic acid sequence encoding a first cell surface transmembrane protein (CSTMP) that comprises an extracellular domain, a transmembrane domain, and an endodomain, (b) B comprises a nucleic acid sequence encoding a second CSTMP that is different from the first CSTMP and comprises an extracellular domain, a transmembrane domain, and an endodomain, and (c) X is a nucleic acid sequence which encodes a cleavage site;

wherein the endodomain of one of the first and the second CSTMP further comprises an intracellular retention signal which directs said protein to an intracellular compartment, such that, when said nucleic acid construct is expressed in a cell, the first and second CSTMP are expressed at the cell surface, with the proviso that the cell surface expression of the CSTMP with the intracellular retention signal is reduced compared to expression from an equivalent construct which does not include the intracellular retention signal;

said intracellular retention signal comprising an endocytosis signal; a Golgi retention signal; a trans-Golgi network (TGN) recycling signal; an endoplasmic reticulum (ER) retention signal; or a lysosomal sorting signal.

2. The nucleic acid construct according to claim 1, wherein the intracellular retention signal is proximal to the transmembrane domain of the CSTMP with the intracellular retention signal.

3. The nucleic acid construct according to claim 1, wherein the intracellular retention signal is distal to the transmembrane domain of the CSTMP with the intracellular retention signal.

4. The nucleic acid construct according to claim 1 wherein X is a nucleic acid sequence encoding a self-cleaving peptide, a furin cleavage site or a Tobacco Etch Virus cleavage site.

5. The nucleic acid construct according to claim 4, wherein X encodes a 2A self-cleaving peptide from an aphtho- or a cardiovirus or a 2A-like peptide.

6. The nucleic acid construct according to claim 1, wherein at least one of the first cell surface transmembrane protein and the second cell surface transmembrane protein is a Chimeric-antigen receptor (CAR).

7. The nucleic acid construct according to claim 1, wherein one or both of the first and the second CSTMP is a single pass transmembrane protein.

8. The nucleic acid construct according to claim 7, wherein one or both of the first and the second CSTMP is a Type I transmembrane protein.

9. A vector comprising the nucleic acid construct according to claim 1.

10. An isolated cell comprising the vector according to claim 9.

11. The vector according to claim 9, wherein the vector comprises a retroviral vector or a lentiviral vector or a transposon.

12. An isolated cell comprising the nucleic acid construct according to claim 1.

13. A nucleic acid construct comprising the following structure:

A-X-B-Y-C in which
(a) each of A B, and C is a nucleic acid sequence encoding a polypeptide of interest (POI), wherein said POI are different proteins, and
(b) X and Y are nucleic acid sequences which may be the same or different, each of which encodes a cleavage site,
wherein at least two of the POIs are cell surface transmembrane proteins (CSTMP) that each comprise an extracellular domain, a transmembrane domain, and an endodomain, and wherein the endodomain of each of said CSTMP further comprises an intracellular retention signal which directs said POI to an intracellular compartment, such that, when said nucleic acid construct is expressed in a cell, the CSTMP are expressed at the cell surface, with the proviso that the cell surface expression of each CSTMP with the intracellular retention signal is reduced compared to expression from an equivalent construct which does not include the intracellular retention signal;

said intracellular retention signals comprising an endocytosis signal; a Golgi retention signal; a trans-Golgi network (TGN) recycling signal; an endoplasmic reticulum (ER) retention signal; or a lysosomal sorting signal.

14. The nucleic acid construct according to claim 13, wherein the at least two POIs which are CSTMP and which comprise an intracellular retention signal:
(a) comprise different intracellular retention signals; and/or
(b) have the intracellular retention signal located at a different position in the POI.

15. A vector comprising the nucleic acid construct according to claim 13.

16. The vector according to claim 15, wherein the vector comprises a retroviral vector or a lentiviral vector or a transposon.

17. An isolated cell comprising the nucleic acid construct according to claim 13.

18. An isolated cell comprising the vector according to claim 15.

19. A method for modulating the relative cell surface expression of a first cell surface transmembrane protein (CSTMP) expressed with a second CSTMP that is different from the first CSTMP from a single nucleic acid construct, the method comprising:
(a) providing the single nucleic acid expression construct containing a nucleotide sequence that encodes the first CSTMP and a nucleotide sequence that encodes the second CSTMP,
wherein the first CSTMP and the second CSTMP each comprises an extracellular domain, a transmembrane domain, an endodomain, and
wherein the endodomain of one of the first CSTMP and the second CSTMP further comprises an intracellular retention signal, wherein the intracellular retention signal directs said CSTMP to an intracellular compartment, such that, when said nucleic acid expression construct is expressed in a cell, the CSTMP with the intracellular retention signal is expressed at the cell surface, with the proviso that the cell surface expression of the CSTMP with the intracellular retention signal is reduced compared to expression from an equivalent construct which does not include the intracellular retention signal,
said intracellular retention signal comprising an endocytosis signal; a Golgi retention signal; a trans-Golgi network (TGN) recycling signal; an endoplasmic reticulum (ER) retention signal; or a lysosomal sorting signal;
(b) transfecting a cell with the nucleic acid expression construct; and
(c) culturing the cell under conditions in which the cell expresses the first cell surface transmembrane protein and the second cell surface transmembrane protein.

* * * * *